(12) United States Patent
Takei

(10) Patent No.: US 8,391,951 B2
(45) Date of Patent: Mar. 5, 2013

(54) MAGNETIC RESONANCE IMAGING APPARATUS AND PROGRAM

(75) Inventor: Naoyuki Takei, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 405 days.

(21) Appl. No.: 12/696,560

(22) Filed: Jan. 29, 2010

(65) Prior Publication Data

US 2010/0198046 A1    Aug. 5, 2010

(30) Foreign Application Priority Data

Jan. 30, 2009 (JP) ................. 2009-020787

(51) Int. Cl.
*A61B 5/055* (2006.01)
(52) U.S. Cl. ......... 600/419; 600/410; 600/413; 324/309
(58) Field of Classification Search .......... 600/410, 600/413, 419; 324/306, 307, 309
See application file for complete search history.

(56) References Cited

U.S. PATENT DOCUMENTS

| | | | |
|---|---|---|---|
| 5,842,989 A | 12/1998 | Zur | |
| 7,030,609 B2 | 4/2006 | Pipe | |
| 7,205,763 B2 | 4/2007 | Porter | |
| 7,323,873 B2 | 1/2008 | Yamazaki | |
| 7,432,710 B2 | 10/2008 | Takei et al. | |
| 7,538,549 B2 | 5/2009 | Takei | |
| 2002/0087067 A1 | 7/2002 | Foo | |
| 2007/0167733 A1* | 7/2007 | Miyoshi | 600/410 |
| 2008/0169808 A1 | 7/2008 | Taniguchi et al. | |
| 2008/0180098 A1 | 7/2008 | Takei | |
| 2009/0005673 A1 | 1/2009 | Rehwald et al. | |
| 2009/0221905 A1 | 9/2009 | Takei | |
| 2009/0270719 A1* | 10/2009 | Miyoshi | 600/413 |
| 2010/0090693 A1* | 4/2010 | Wald et al. | 324/307 |

OTHER PUBLICATIONS

Mitsue Miyazaki et al, Recent Development of Non-Contrast-Enhanced MR Angiography, Image Information Medical, Sangyo Kaihatsukiko, Sep. 2006, pp. 952-957.
Non-Final Office Action dated Mar. 16, 2012, U.S. Appl. No. 12/392,225; 18 pages.
Talagala et al., Whole-Brain 3D Perfusion MRI at 3.0 T Using CASL With a Separate Labeling Coil, Magnetic Resonance in Medicine 52:131-140 (2004).
Simonetti et al., "Black Blood" T2-weighted Inversion Recovery MR Imaging of the Heart, Radiology 199:49-57 (1996).

* cited by examiner

*Primary Examiner* — Ruth S Smith
(74) *Attorney, Agent, or Firm* — Armstrong Teasdale LLP

(57) ABSTRACT

A magnetic resonance imaging apparatus includes a gradient coil for applying a gradient pulse, a transmitting coil for transmitting an RF pulse, and a coil control device for controlling the gradient coil and the transmitting coil in such a manner that a pulse sequence for (A) making an absolute value of longitudinal magnetization of a first background tissue and an absolute value of longitudinal magnetization of a second background tissue longer in T1 value than the first background tissue smaller than an absolute value of longitudinal magnetization of body fluid of a subject, (B) acquiring magnetic resonance signals from the subject, and (C) flipping transverse magnetization of the second background tissue to longitudinal magnetization is repeatedly executed.

19 Claims, 29 Drawing Sheets

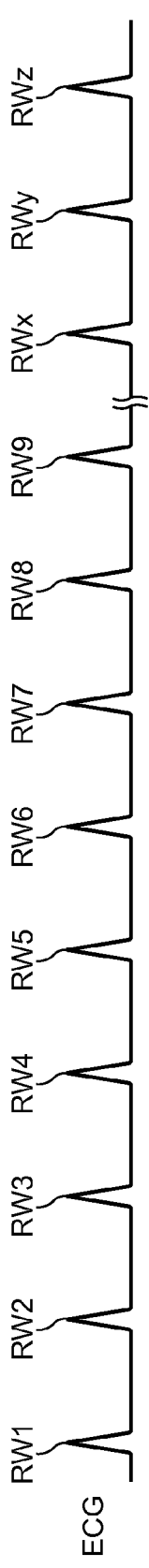
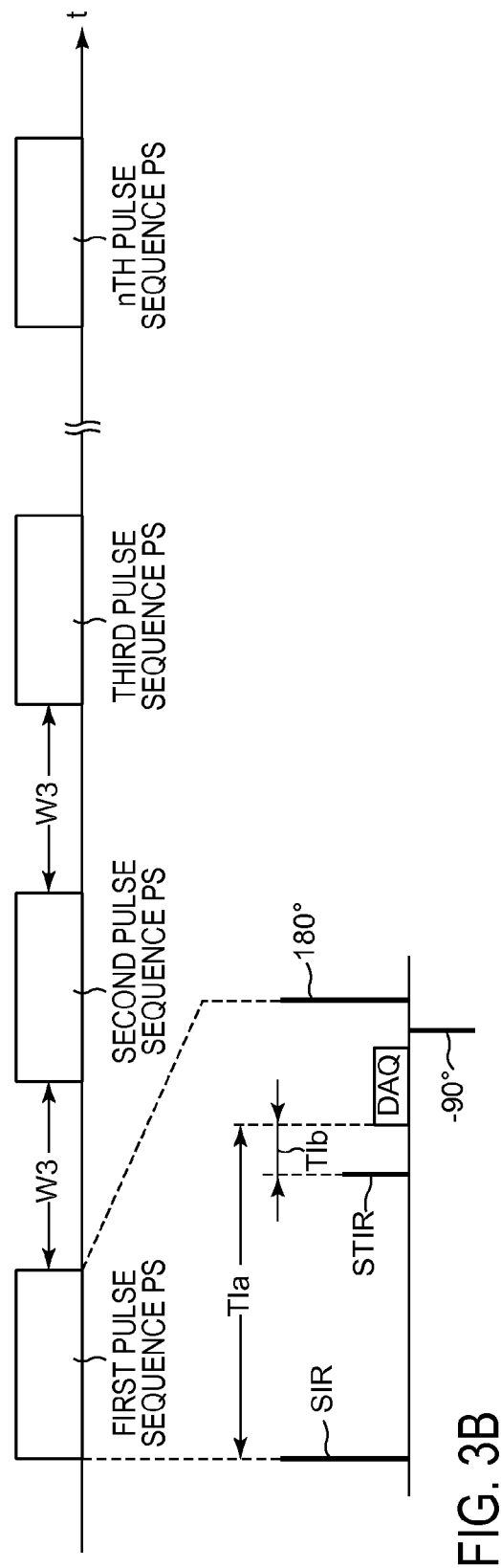
FIG. 3A
FIG. 3B

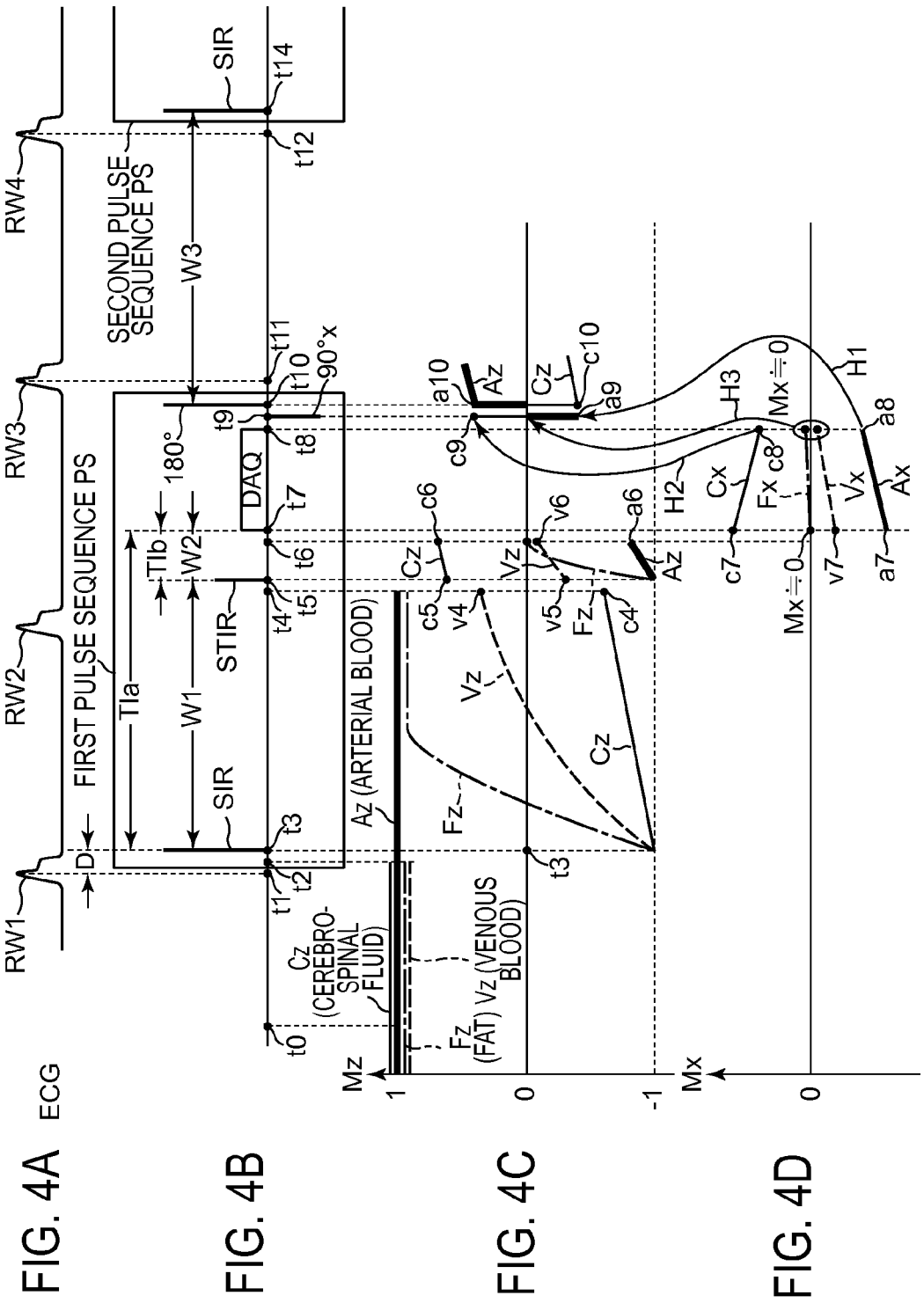

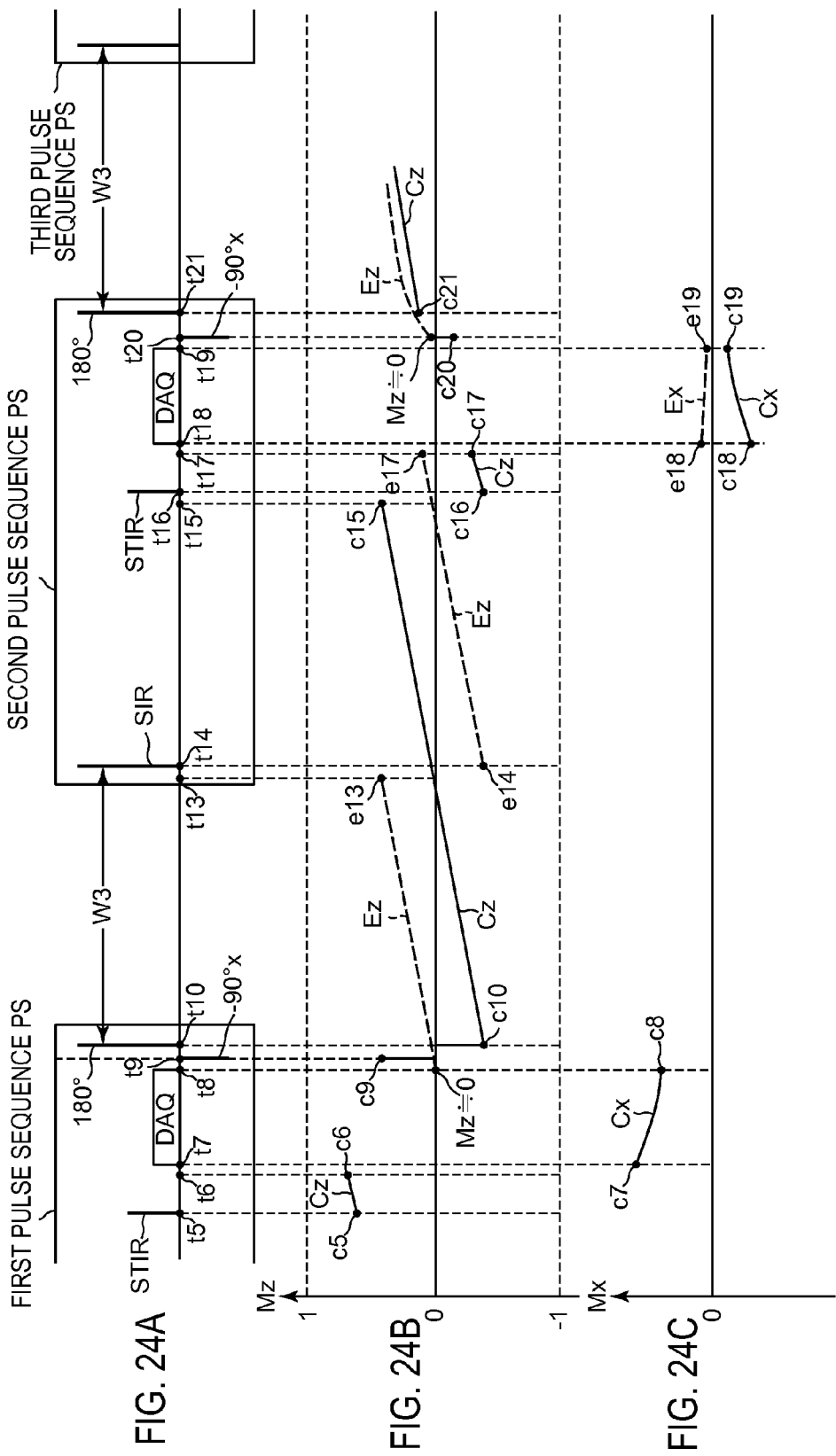

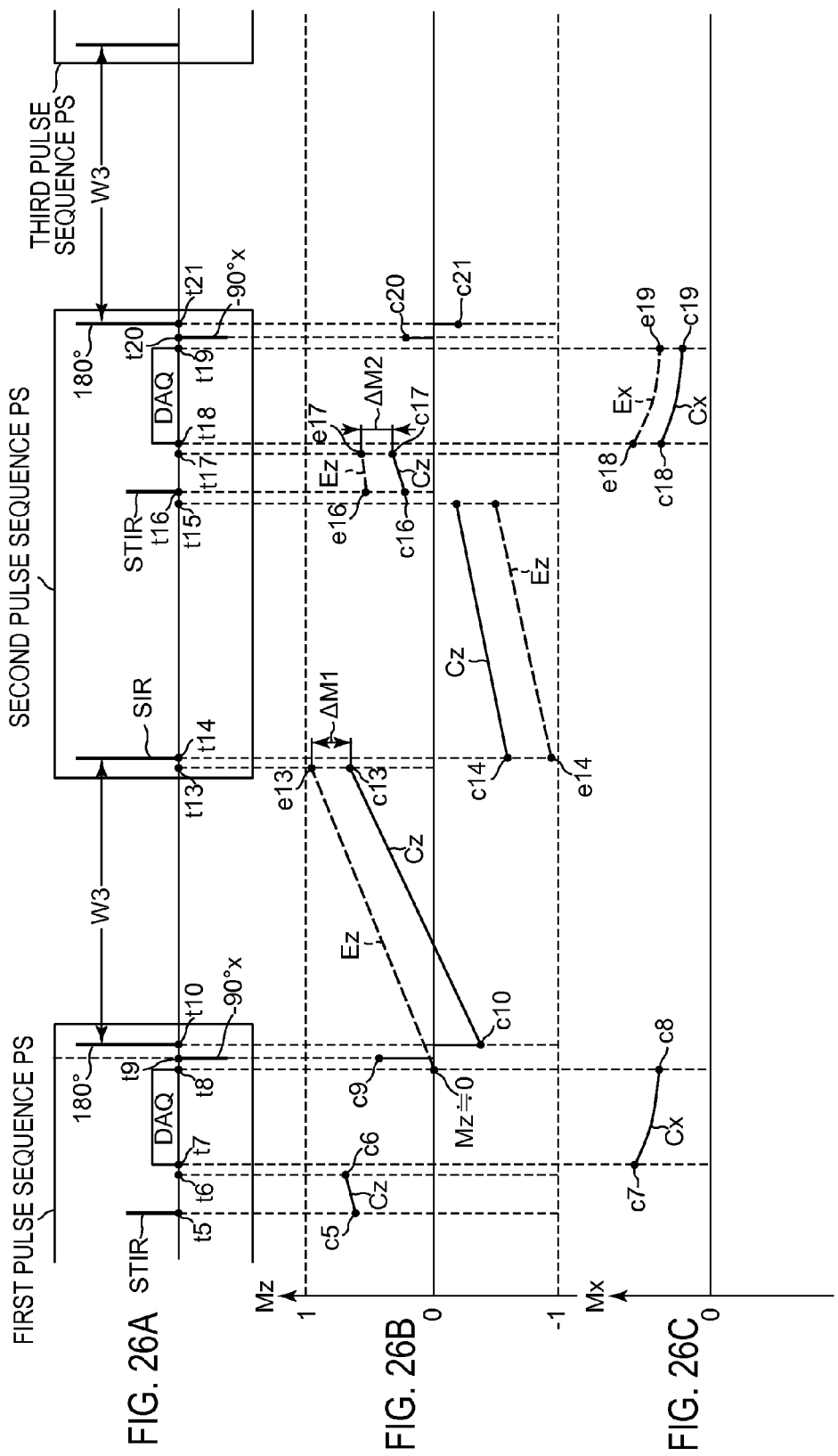

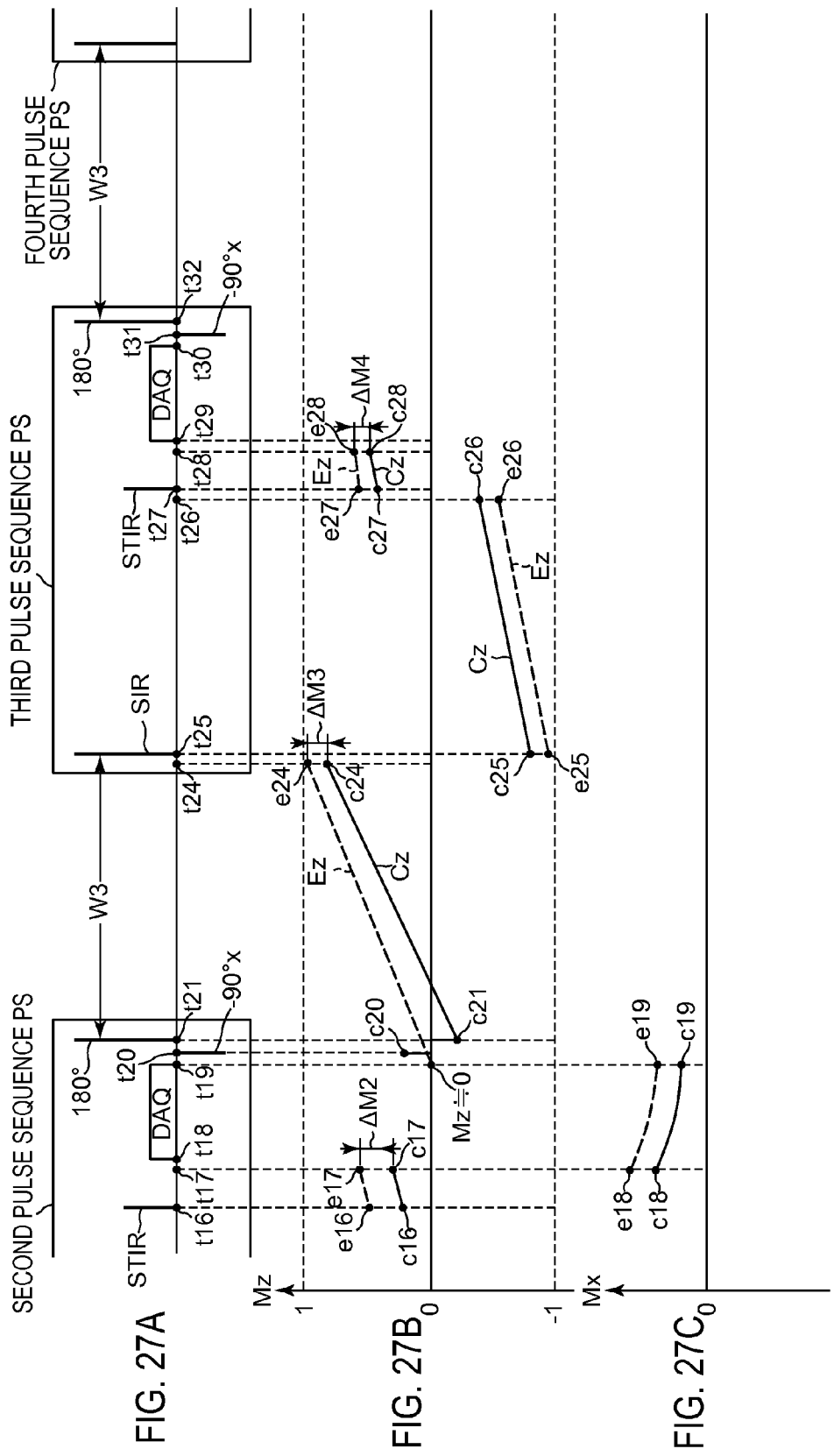

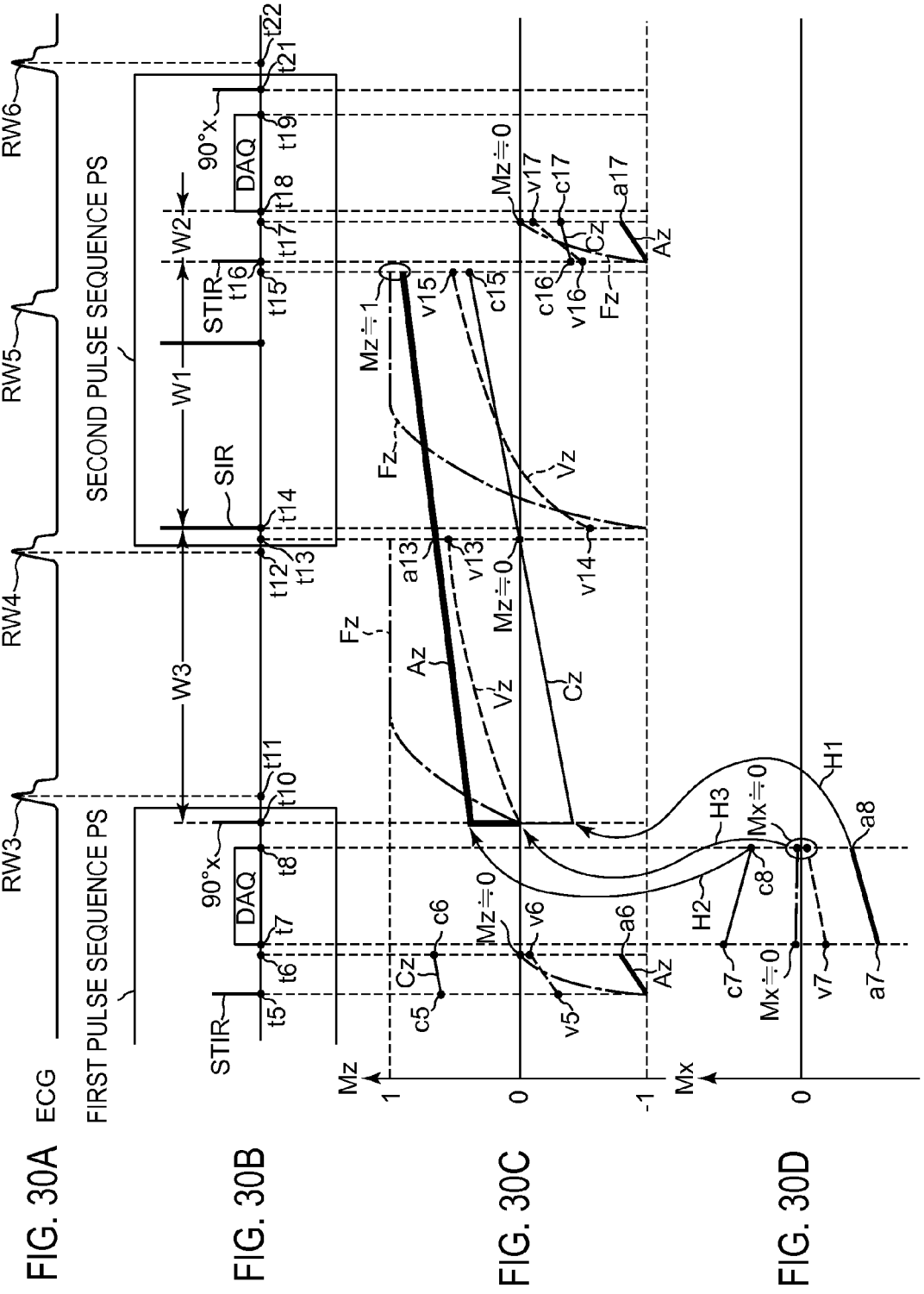

MAGNETIC RESONANCE IMAGING APPARATUS AND PROGRAM

CROSS REFERENCE TO RELATED APPLICATIONS

This application claims the benefit of Japanese Patent Application No. 2009-020787 filed Jan. 30, 2009, which is hereby incorporated by reference in its entirety.

BACKGROUND OF THE INVENTION

The embodiments described herein relate to a magnetic resonance imaging apparatus for imaging a subject and a program therefore.

BACKGROUND ART

As a method for visualizing arterial blood of the head of a subject, there has been known MRA (Magnetic Resonance Angiography) for visualizing a blood flow of a subject without using a contrast agent. As one example of MRA, there has been known, for example, a Time-SLIP method (refer to Mitsue Miyazaki and six more inventors "Recent Development of Non-Contrast-Enhanced MRAngiography", Image Information Medical, Sangyo Kaihatsukiko Inc., September Issue, 2006, p. 952-957).

Since it becomes hard to visually identify arterial blood when background tissues (such as fat and cerebrospinal fluid) are visualized together in addition to the arterial blood, there occurs a case where it is not desired to visualize the background tissues as much as possible. The method according to the non-patent document 1 is however accompanied by a problem that there is a need to create a difference image in order to obtain an MRA image in which background tissues such as cerebrospinal fluid have been suppressed, and an imaging time is hence taken therefor.

BRIEF DESCRIPTION OF THE INVENTION

In one aspect, a magnetic resonance imaging apparatus is provided, including: a gradient coil for applying a gradient pulse; a transmitting coil for transmitting an RF pulse; and a coil control device for controlling the gradient coil and the transmitting coil in such a manner that a pulse sequence for (A) making an absolute value of longitudinal magnetization of a first background tissue and an absolute value of longitudinal magnetization of a second background tissue longer in T1 value than the first background tissue, smaller than an absolute value of longitudinal magnetization of body fluid of a subject, (B) acquiring magnetic resonance signals from the subject, and (C) flipping transverse magnetization of the second background tissue to longitudinal magnetization is repeatedly executed.

In another aspect, a program is provided for controlling a magnetic resonance imaging apparatus having a gradient coil for applying a gradient pulse and a transmitting coil for transmitting an RF pulse, the program being used to repeatedly execute a pulse sequence for (A) making an absolute value of longitudinal magnetization of a first background tissue and an absolute value of longitudinal magnetization of a second background tissue longer in T1 value than the first background tissue, smaller than an absolute value of longitudinal magnetization of body fluid of a subject, (B) acquiring magnetic resonance signals from the subject, and (C) flipping transverse magnetization of the second background tissue to longitudinal magnetization.

In some embodiments, the absolute values of longitudinal magnetization of first and second background tissues are set smaller than the absolute value of longitudinal magnetization of body fluid before the acquisition of magnetic resonance signals. Accordingly, an image can be obtained in which the first background tissue and the second background tissue have been suppressed.

In some embodiments, transverse magnetization of a second background tissue long in T1 value is flipped to longitudinal magnetization before the execution of the following pulse sequence after the acquisition of magnetic resonance signals. Consequentially, the second background tissue long in T1 value can be suppressed efficiently even though variations occur in a waiting time from the end of a pulse sequence to the start of the following pulse sequence.

Since there is obtained an image in which the longitudinal magnetization of first and second background tissues are suppressed, even though a difference image is not created, the shortening of an imaging time can be achieved.

Further embodiments of the present invention will be apparent from the following description of the preferred embodiments of the invention as illustrated in the accompanying drawings.

BRIEF DESCRIPTION OF THE DRAWINGS

FIGS. 3A and 3B are diagrams for describing each pulse sequence for obtaining an MR image in which arterial blood is visualized emphatically and background tissues are suppressed as much as possible.

FIGS. 4A, 4B, 4C, and 4D are diagrams for explaining how magnetization of each tissue lying within the imaging surface changes according to a first pulse sequence PS.

FIGS. 24A, 24B, and 24C are diagrams for describing how the magnetization of cerebrospinal fluid changes from the end of a first pulse sequence PS to the end of a second pulse sequence PS with a waiting time W3 (=1200 msec) interposed therebetween.

FIGS. 26A, 26B, and 26C are diagrams for describing how the magnetization of cerebrospinal fluid changes from the end of a first pulse sequence PS to the end of a second pulse sequence PS with a waiting time W3 (=4000 msec) interposed therebetween.

FIGS. 27A, 27B, and 27C are diagrams for describing how the magnetization of cerebrospinal fluid changes from the end of a second pulse sequence PS to the end of a third pulse sequence PS with a waiting time W3 (=4000 msec) interposed therebetween.

FIGS. 30A, 30B, 30C, and 30D are diagrams showing the behaviors of magnetization of arterial blood and background tissues (cerebrospinal fluid, fat and venous blood) where the pulse sequence PS1 shown in FIG. 29 is used.

DETAILED DESCRIPTION OF THE INVENTION

Although a mode for carrying out the invention will hereinafter be explained, the invention is not limited to the following mode.

Figure 1:
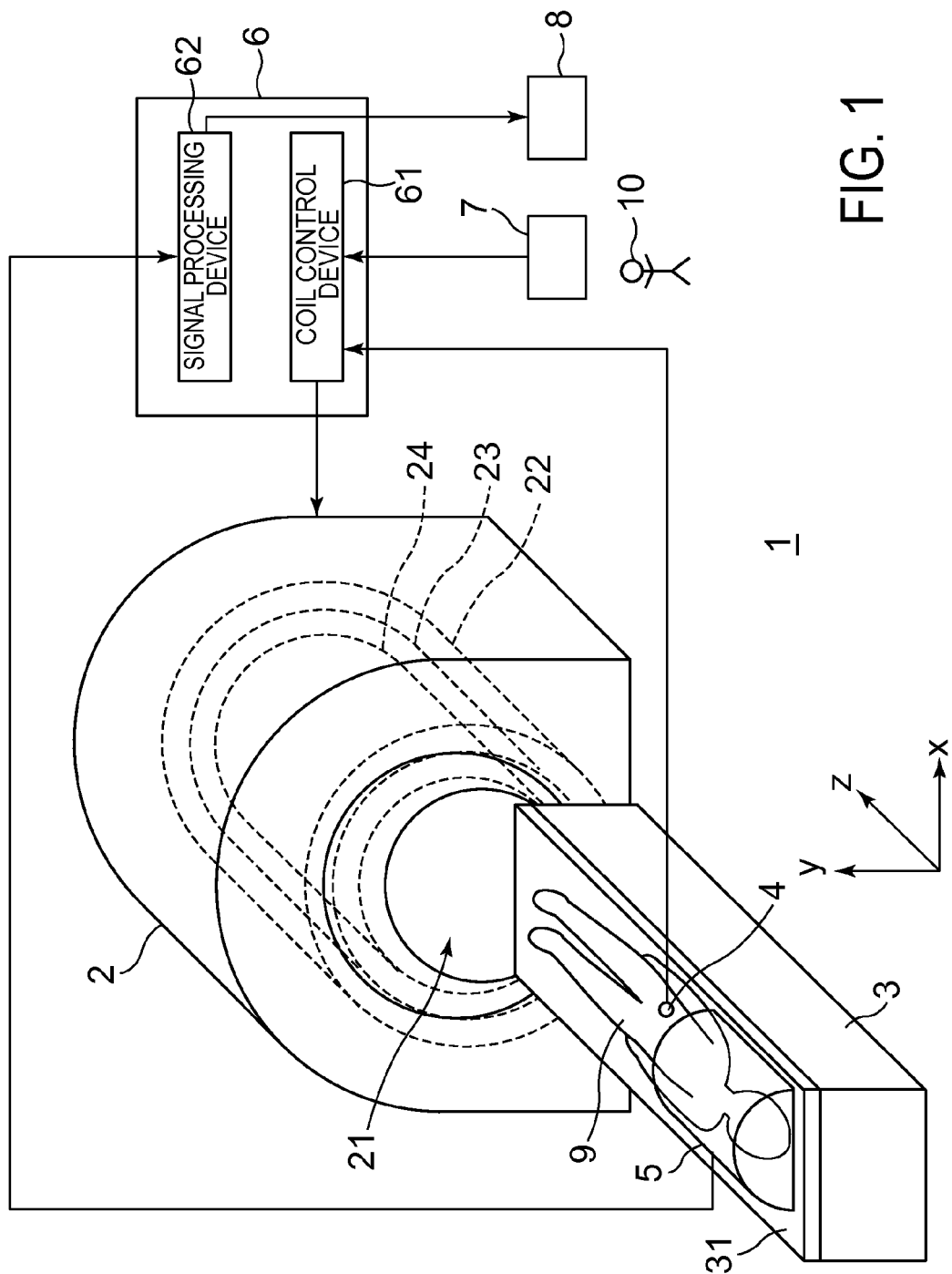
FIG. 1 is a schematic diagram of a magnetic resonance imaging apparatus 1 according to one embodiment of the invention.

FIG. 1 is a schematic diagram of a magnetic resonance imaging apparatus 1 according to one embodiment of the invention.

The magnetic resonance imaging apparatus (hereinafter called "MRI (Magnetic Resonance Imaging) system") 1 has a coil assembly 2, a table 3, a heartbeat sensor 4, a receiving coil 5, a controller 6, an input device 7 and a display device 8.

The coil assembly 2 has a bore 21 in which a subject 9 is accommodated, a superconductive coil 22, a gradient coil 23 and a transmitting coil 24. The superconductive coil 22 applies a static magnetic field BO, the gradient coil 23 applies a gradient pulse and the transmitting coil 24 transmits an RF pulse.

The table 3 has a cradle 31. The cradle 31 is configured so as to move in a z direction and a −z direction. With the movement of the cradle 31 in the z direction, the subject 9 is conveyed to the bore 21. With the movement of the cradle 31 in the −z direction, the subject 9 conveyed to the bore 21 is carried out of the bore 21.

The heartbeat sensor 4 detects the heartbeat of the subject 9 and transmits an electrocardiac signal ECG to the coil control device 61.

The receiving coil 5 is attached from the head of the subject 9 to the chest thereof. An MR (Magnetic Resonance) signal received by the receiving coil 5 is transmitted to the controller 6.

The controller 6 has a coil control device 61 and a signal processing device 62.

The coil control device 61 controls the gradient coil 23 and the transmitting coil 24 based on an imaging command inputted from the input device 7 and the electrocardiac signal ECG outputted from the heartbeat sensor 4 in such a manner that a pulse sequence PS (refer to FIG. 3B) for acquiring magnetic resonance signals from the subject 9 is repeatedly executed. The coil control device 61 is realized by installing a program for repeatedly executing each pulse sequence PS in the controller 6, based on the electrocardiac signal ECG outputted from the heartbeat sensor 4. It may however be implemented by only hardware without using the program.

The signal processing device 62 processes an MR signal sent from the receiving coil 5 to reconstruct an image.

The input device 7 transmits various commands or the like to the controller 6 in accordance with the operation of an operator 10.

The display device 8 displays images or the like thereon.

The subject 9 is imaged using the MRI system 1 configured as described above.

Figure 2:
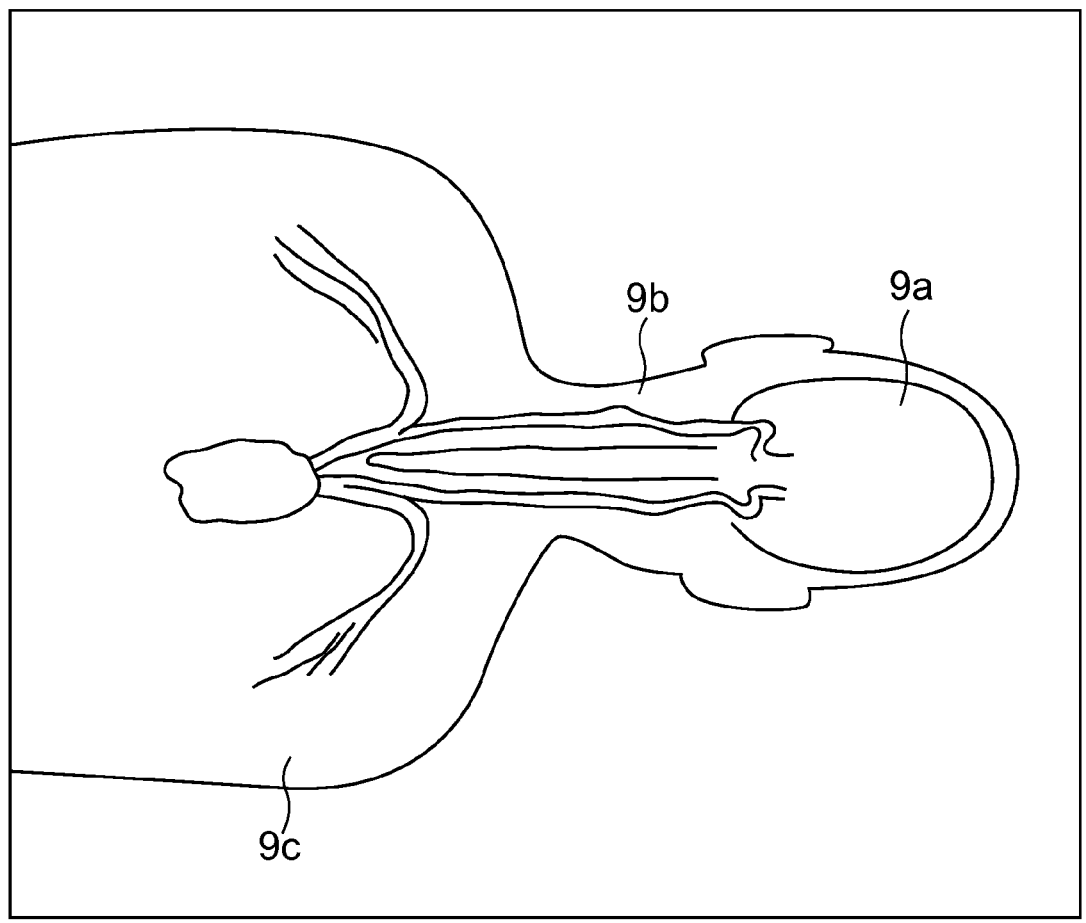
FIG. 2 is a diagram showing one example of an imaging surface of a subject 9.

FIG. 2 is a diagram showing one example of an imaging surface of the subject 9.

In the present embodiment, the head 9a, neck 9b and chest 9c of the subject 9 are imaged. In the MRI system 1, a pulse sequence for obtaining an MR image in which arterial blood is visualized emphatically and background tissues are suppressed as much as possible is executed based on the electrocardiac signal ECG of the subject 9. One example of this pulse sequence will be explained below.

FIGS. 3A and 3B are diagrams for describing each pulse sequence for obtaining an MR image in which arterial blood is visualized emphatically and background tissues are suppressed as much as possible.

FIG. 3A is a diagram showing the timing at which each pulse sequence PS is executed on the electrocardiac signal ECG.

The pulse sequence PS is of a pulse sequence capable of visualizing arterial blood emphatically and suppressing background tissues (venous blood and muscles, for example). The pulse sequence PS is repeatedly executed in synchronization with each R wave of the electrocardiac signal ECG. A waiting time W3 (refer to FIG. 4B to be described later) that varies according to an R-R interval defined between the adjacent R waves of the subject is provided between the pulse sequence PS and the following pulse sequence PS.

FIG. 3B is a diagram showing one example of the pulse sequence PS.

The pulse sequence PS has a selective inversion pulse SIR (Selective Inversion Recovery), a fat suppression pulse STIR (Short Tau Inversion Recovery), a signal acquisition sequence DAQ, a −90° x pulse and a 180° pulse.

The selective inversion pulse SIR is of a pulse for inverting longitudinal magnetization of each tissue in a region R1 (refer to FIG. 5 to be described later) of an imaging surface of a subject. The fat suppression pulse STIR is of a pulse for inverting longitudinal magnetization of each tissue lying in the entire imaging surface of the subject. With the combination of the selective inversion pulse SIR and the fat suppression pulse STIR, the longitudinal magnetization of plural background tissues (such as fat, venous blood and the like) can be made closer to a null point than the longitudinal magnetization of arterial blood up to immediately before the execution of the signal acquisition sequence DAQ. An inversion time TIa of the selective inversion pulse SIR is of a value that ranges from about 1200 msec to about 1300 msec, for example. An inversion time TIb of the fat suppression pulse STIR is of a value that ranges from about 175 msec to about 185 msec, for example.

The signal acquisition sequence DAQ is of a sequence for acquiring magnetic resonance signals from the subject. An FSE (Fast Spin Echo) method, a GRE (Gradient Echo) method or the like can be used for the sequence. In the present embodiment, its description will be continued as the sequence using the FSE method.

The −90° x pulse is of an FS (Fast Recovery) pulse for flipping transverse magnetization of each tissue to longitudinal magnetization. The 180° pulse is of a pulse for inverting the longitudinal magnetization. A description will be made later of what advantage can be brought about by the combination of the −90° x pulse and the 180° pulse.

A description will next be made of how the magnetization of each tissue lying within a subject's imaging surface changes while the pulse sequence PS shown in FIGS. 3A and 3B is being executed repeatedly. A description will first be made below of how the magnetization of each tissue lying within the imaging surface changes according to a first pulse sequence PS.

FIGS. 4A-4D are diagrams for describing how the magnetization of each tissue lying within the imaging surface changes according to the first pulse sequence PS.

FIG. 4A is a diagram showing R waves RW1 through RW3 of an electrocardiac signal ECG, FIG. 4B is a diagram showing the first pulse sequence PS executed during the R waves RW1 through RW3, FIG. 4C is a diagram showing a change in longitudinal magnetization of each tissue with time, and FIG. 4D is a diagram showing a change in transverse magnetization of each tissue with time, respectively.

Four longitudinal magnetization recovery curves Az, Cz, Fz and Vz are shown in FIG. 4C. The longitudinal magnetization recovery curves Az, Cz, Fz and Vz are respectively indicated by a thick solid line, a thin solid line, a one-dot chain line and a broken line. The longitudinal magnetization recovery curves Az, Cz, Fz and Vz are respectively curves indicative of changes in longitudinal magnetization of arterial blood, cerebrospinal fluid, fat and venous blood with time.

Four transverse magnetization recovery curves Ax, Cx, Fx and Vx are shown in FIG. 4D. The transverse magnetization recovery curves Ax, Cx, Fx and Vx are respectively indicated by a thick solid line, a thin solid line, a one-dot chain line and a broken line. The transverse magnetization recovery curves Ax, Cx, Fx and Vx are respectively curves indicative of changes in transverse magnetization of arterial blood, cerebrospinal fluid, fat and venous blood with time.

The longitudinal magnetization recovery curves Az, Cz, Fz and Vz and the transverse magnetization recovery curves Ax, Cx, Fx and Vx will be explained below for every t0, . . . , t10 of times.

(1) Times t0 to t2

Figure 5:
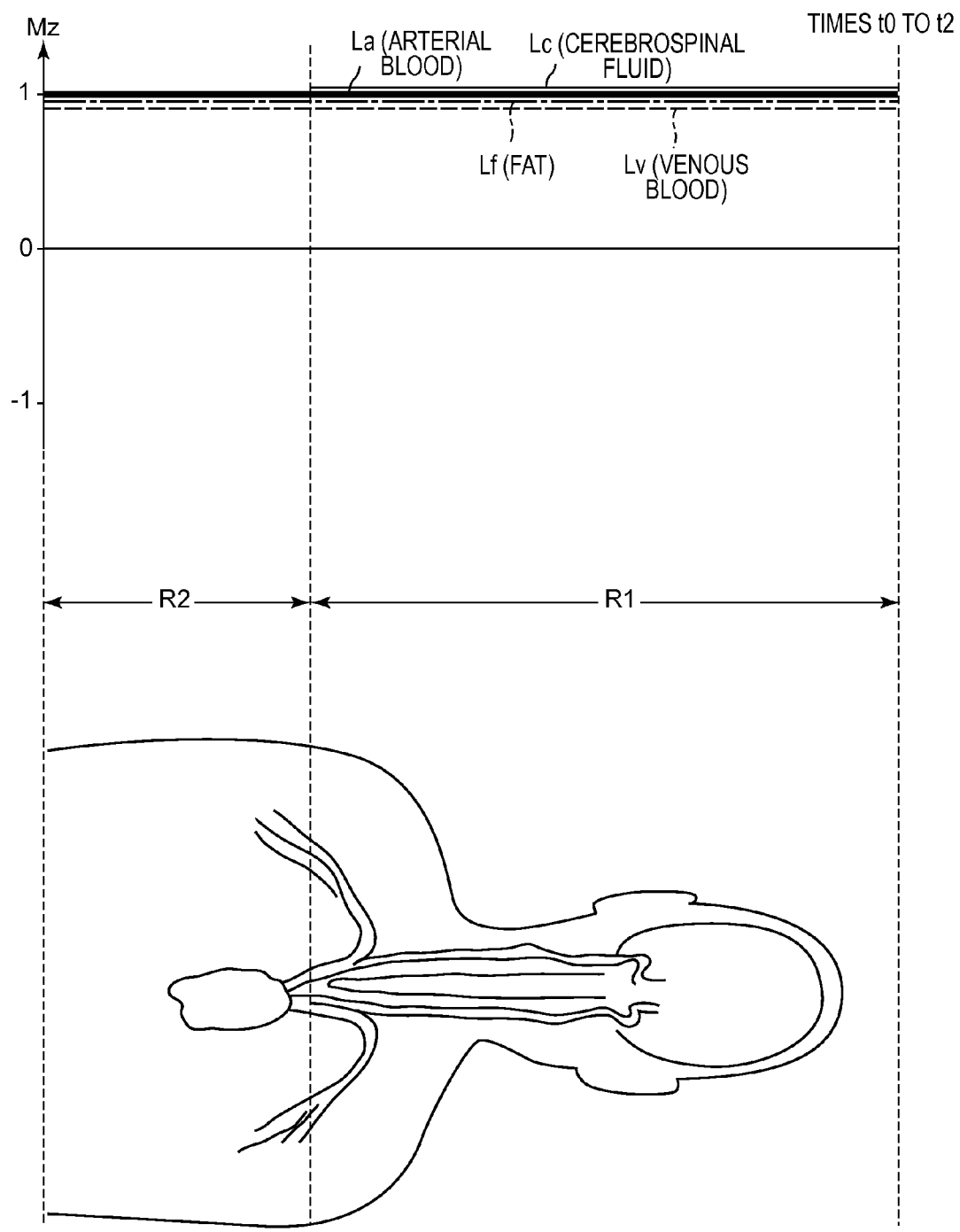
FIG. 5 is a diagram showing longitudinal magnetization Mz of arterial blood, cerebrospinal fluid, fat and venous blood lying within the imaging surface between times t0 and t2.

FIG. 5 is a diagram showing longitudinal magnetization Mz of arterial blood, cerebrospinal fluid, fat and venous blood lying within the imaging surface between the times t0 and t2.

Four lines La, Lc, Lf and Lv are shown in FIG. 5. The line La (thick solid line) indicates the longitudinal magnetization of arterial blood lying with the imaging surface. The line Lc (thin solid line) indicates the longitudinal magnetization of cerebrospinal fluid lying within the imaging surface. The line Lf (one-dot chain line) indicates the longitudinal magnetization of fat lying within the imaging surface. The line Lv (broken line) indicates the longitudinal magnetization of venous blood lying within the imaging surface.

While, however, the imaging surface crosses the position where the cerebrospinal fluid exists in a region R1, it does not cross the position where the cerebrospinal fluid exists in a region R2. Thus, the line Lc indicative of the longitudinal magnetization of the cerebrospinal fluid is shown only in the region R1, but is not shown in the region R2.

The pulse sequence PS has not yet been executed between the times t0 and t2. Thus, the longitudinal magnetization Mz of each of the arterial blood, cerebrospinal fluid, fat and venous blood at the time t0 is Mz=1.

(2) Time t3

When the R wave RW1 of the electrocardiac signal ECG is detected, the coil control device 61 (refer to FIG. 1) controls the gradient coil 23 and the transmitting coil 24 in synchronization with the R wave RW1 in such a manner that a first pulse sequence PS is executed. When the first pulse sequence PS is started, a selective inversion pulse SIR is transmitted at the time t3 at which a delay time D has elapsed from the R wave RW1 (time t1). With the transmission of the selective inversion pulse SIR, the longitudinal magnetization Mz of each of arterial blood and background tissues (cerebrospinal fluid, fat and venous blood) changes in the following manner (refer to FIG. 6).

Figure 6:
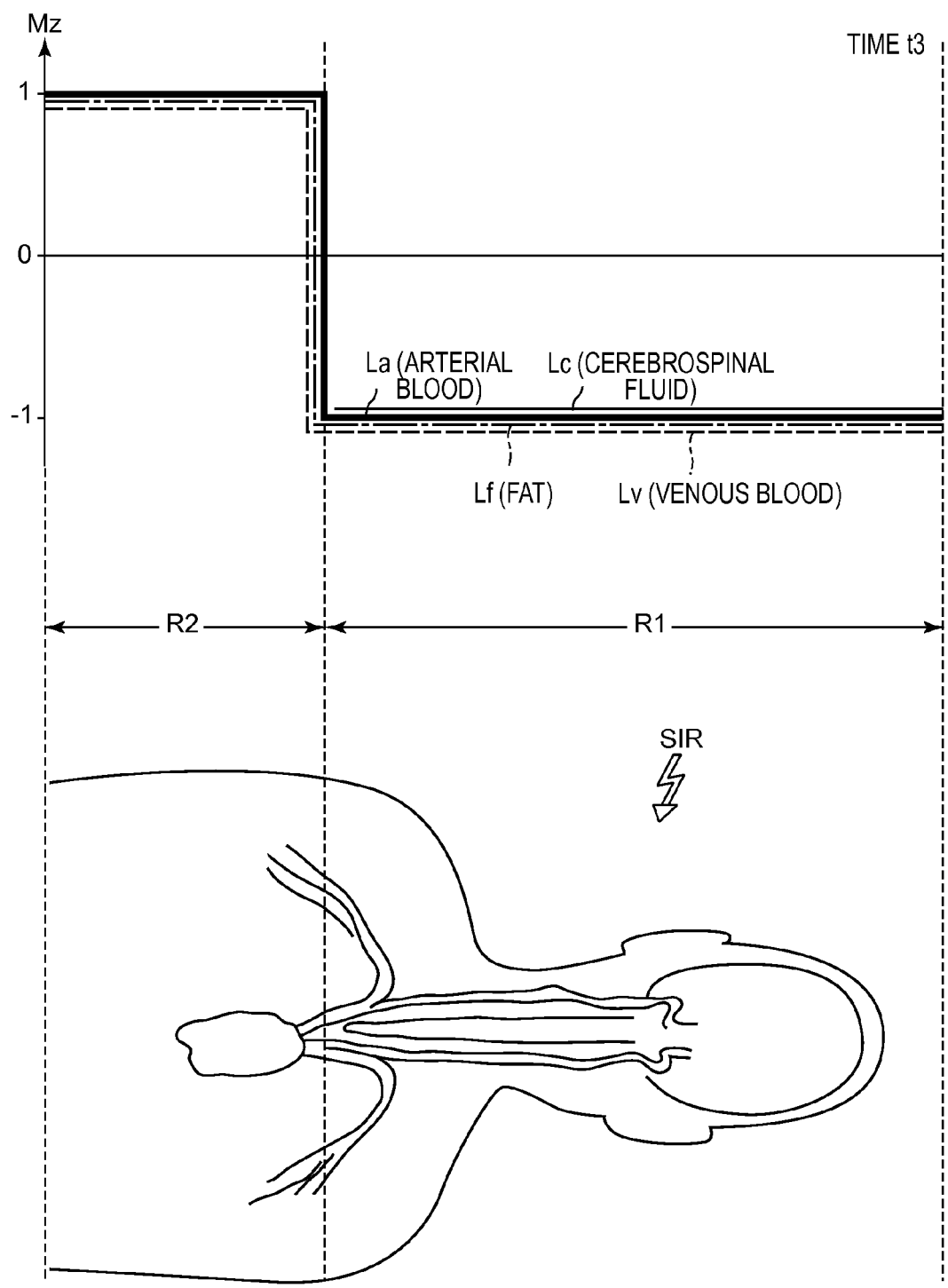
FIG. 6 is a diagram illustrating longitudinal magnetization Mz of arterial blood, cerebrospinal fluid, fat and venous blood lying within the imaging surface at a time t3.

FIG. 6 is a diagram showing the longitudinal magnetization Mz of arterial blood, cerebrospinal fluid, fat and venous blood lying within the imaging surface at the time t3.

A description will be made below of how the longitudinal magnetization Mz of each of arterial blood and background tissues (cerebrospinal fluid, fat and venous blood) changes with the transmission of the selective inversion pulse SIR while referring to FIG. 6.

(i) Longitudinal Magnetization Mz of Arterial Blood

The selective inversion pulse SIR is of a selective pulse for inverting the longitudinal magnetization of each tissue lying within the region R1 (region containing the head and neck of the subject) and avoiding the inversion of the longitudinal magnetization of each tissue lying within the region R2 (region containing the heart of the subject). Thus, the longitudinal magnetization Mz of arterial blood in the region R1 is inverted from Mz=1 to Mz=−1 as shown in FIG. 6 by the transmission of the selective inversion pulse SIR.

On the other hand, since the longitudinal magnetization Mz of arterial blood in the region R2 is not affected by the selective inversion pulse SIR, the longitudinal magnetization Mz remains at Mz=1 even at the time t3 as shown in FIG. 6. The longitudinal magnetization recovery curve Az shown in FIG. 4C concretely shows the manner in which the longitudinal magnetization Mz of arterial blood in the region R2 remains at Mz=1 at the time t3 without being affected by the selective inversion pulse SIR (incidentally, the manner in which the longitudinal magnetization Mz of arterial blood in the region R1 is inverted from Mz=1 to Mz=−1, is not shown in FIG. 4C)).

(ii) Longitudinal Magnetization Mz of Background Tissues (Cerebrospinal Fluid, Fat and Venous Blood)

The longitudinal magnetization Mz of each of the background tissues (cerebrospinal fluid, fat and venous blood) in the region R1 is also inverted from Mz=1 to Mz=−1 as shown in FIG. 6 by the transmission of the selective inversion pulse SIR in a manner similar to the longitudinal magnetization Mz of arterial blood.

On the other hand, since the longitudinal magnetization Mz of each of fat and venous blood in the region R2 is not affected by the selective inversion pulse SIR, the longitudinal magnetization Mz remains at Mz=1 even at the time t3 as shown in FIG. 6. The longitudinal magnetization recovery curves Cz, Fz and Vz shown in FIG. 4C respectively concretely show the manner in which the longitudinal magnetization Mz of cerebrospinal fluid, fat and venous blood in the region R1 are inverted from Mz=1 to Mz=−1 by the selective inversion pulse SIR (time t3) (incidentally, the manner in which the longitudinal magnetization Mz of each of fat and venous blood in the region R2 is not changed while remaining at Mz=1, is not shown in FIG. 4C).

(3) Times t3 to t4

After the selective inversion pulse SIR has been transmitted at the time t3, a fat suppression pulse STIR is transmitted at the time t5. A waiting time W1 (=TIa−TIb) is however provided between the times t3 and t5 (refer to FIG. 4B). Thus, longitudinal relaxation proceeds during the waiting time W1, and the longitudinal magnetization Mz of each tissue is represented in the following manner at the time t4 lying immediately before the transmission of the fat suppression pulse STIR.

Figure 7:
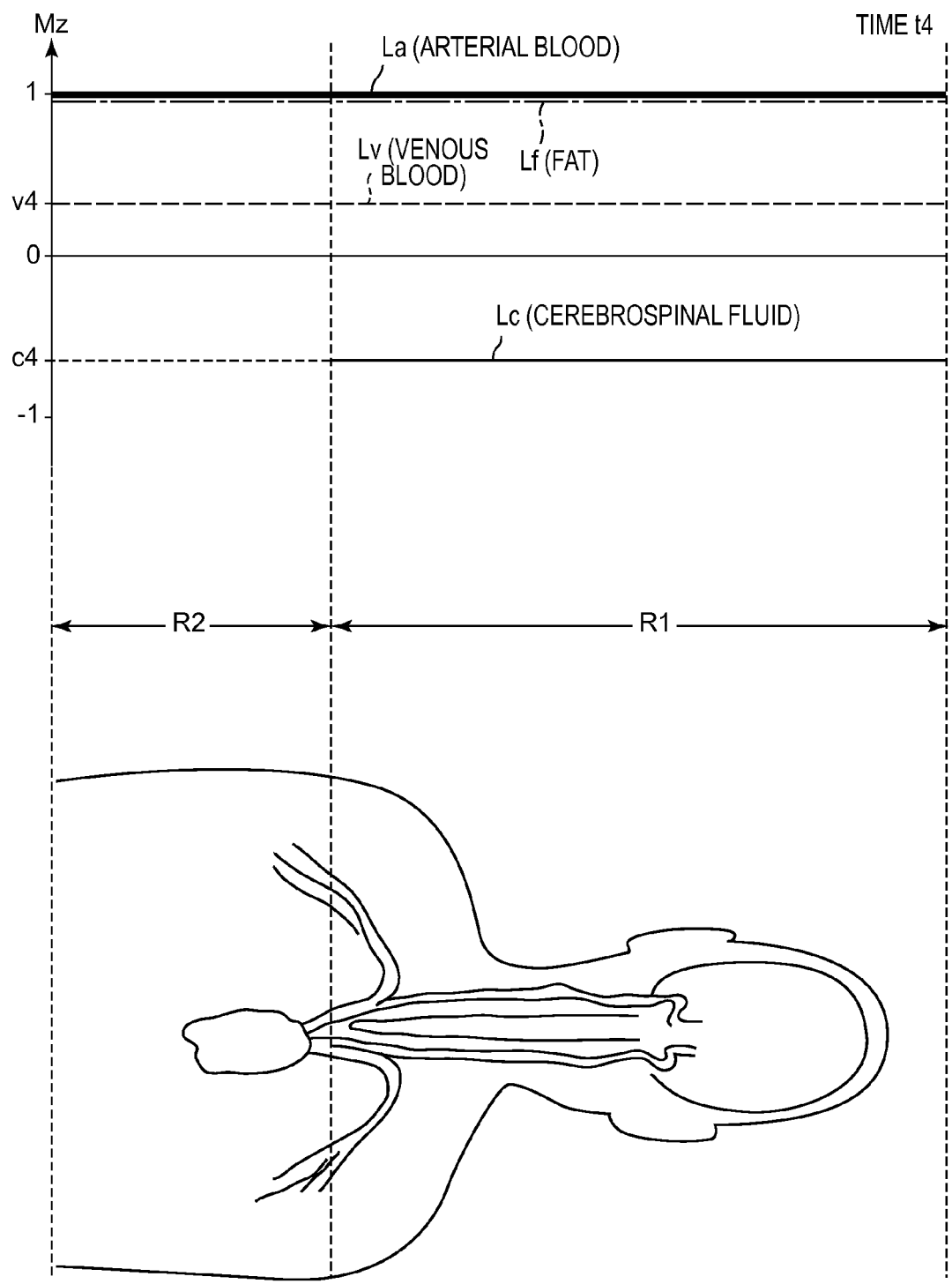
FIG. 7 is a diagram showing longitudinal magnetization Mz of arterial blood, cerebrospinal fluid, fat and venous blood lying within the imaging surface at a time t4.

FIG. 7 is a diagram showing the longitudinal magnetization Mz of arterial blood, cerebrospinal fluid, fat and venous blood lying within the imaging surface at the time t4.

A description will be made below of how the longitudinal magnetization Mz of each of arterial blood and background tissues (cerebrospinal fluid, fat and venous blood) changes during the waiting time W1 while referring to FIG. 7.

(i) Longitudinal Magnetization Mz of Arterial Blood

The longitudinal magnetization Mz of arterial blood in the region R2 is Mz=1 at the time t3 (refer to FIG. 6). Thus, the longitudinal magnetization Mz of arterial blood in the region R2 remains at Mz=1 even at the time t4 as shown in FIG. 7.

Since the arterial blood in the region R2 is pumped from the heart and flows toward the brain, the arterial blood in the region R2 flows into the region R1 during the waiting time W1. Since the longitudinal magnetization Mz of arterial blood in the region R2 is Mz=1 at the time t4 as shown in FIG. 7, the arterial blood in the region R2 flows into the region R1, so that the arterial blood in the region R1 as well as the arterial blood in the region R2 becomes Mz=1 at the time t4.

(ii) Longitudinal Magnetization Mz of Background Tissues (Cerebrospinal Fluid, Fat and Venous Blood)

While the longitudinal magnetization Mz of each of background tissues (cerebrospinal fluid, fat and venous blood) in the region R1 is Mz=−1 at the time t3 (refer to FIG. 6), the longitudinal magnetization Mz is gradually recovered during the waiting time W1. Since the fat is small in T1 value, the longitudinal magnetization Mz of the fat is recovered up to Mz=1 at the time t4 as shown in FIG. 7 (refer to the longitudinal magnetization recovery curve Fz of FIG. 4C). Since the cerebrospinal fluid is large in T1 value, the longitudinal magnetization Mz thereof is recovered only to Mz=c4 at the time t4 (refer to the longitudinal magnetization recovery curve Cz of FIG. 4C). Since the T1 value of the venous blood is of a value between those for the fat and cerebrospinal fluid, the longitudinal magnetization thereof is recovered to Mz=v4 at the time t4 (refer to the longitudinal magnetization recovery curve Vz of FIG. 4C). Incidentally, since the venous blood in the region R1 flows into the region R2 during the waiting time W1, the longitudinal magnetization Mz of venous blood in the region R2 is also brought to Mz=v4 at the time t4.

The longitudinal magnetization Mz of fat in the region R2 is Mz=1 at the time t3 (refer to FIG. 6). Thus, the longitudinal magnetization Mz of fat in the region R2 remains at Mz=1 at the time t4 as shown in FIG. 7.

(4) Time t5

At the time t5, a fat suppression pulse STIR (refer to FIG. 4B) in a pulse sequence PS1 is transmitted. With the transmission of the fat suppression pulse STIR, the longitudinal magnetization Mz of each of arterial blood and background tissues (cerebrospinal fluid, fat and venous blood) changes as follows (refer to FIG. 8).

Figure 8:
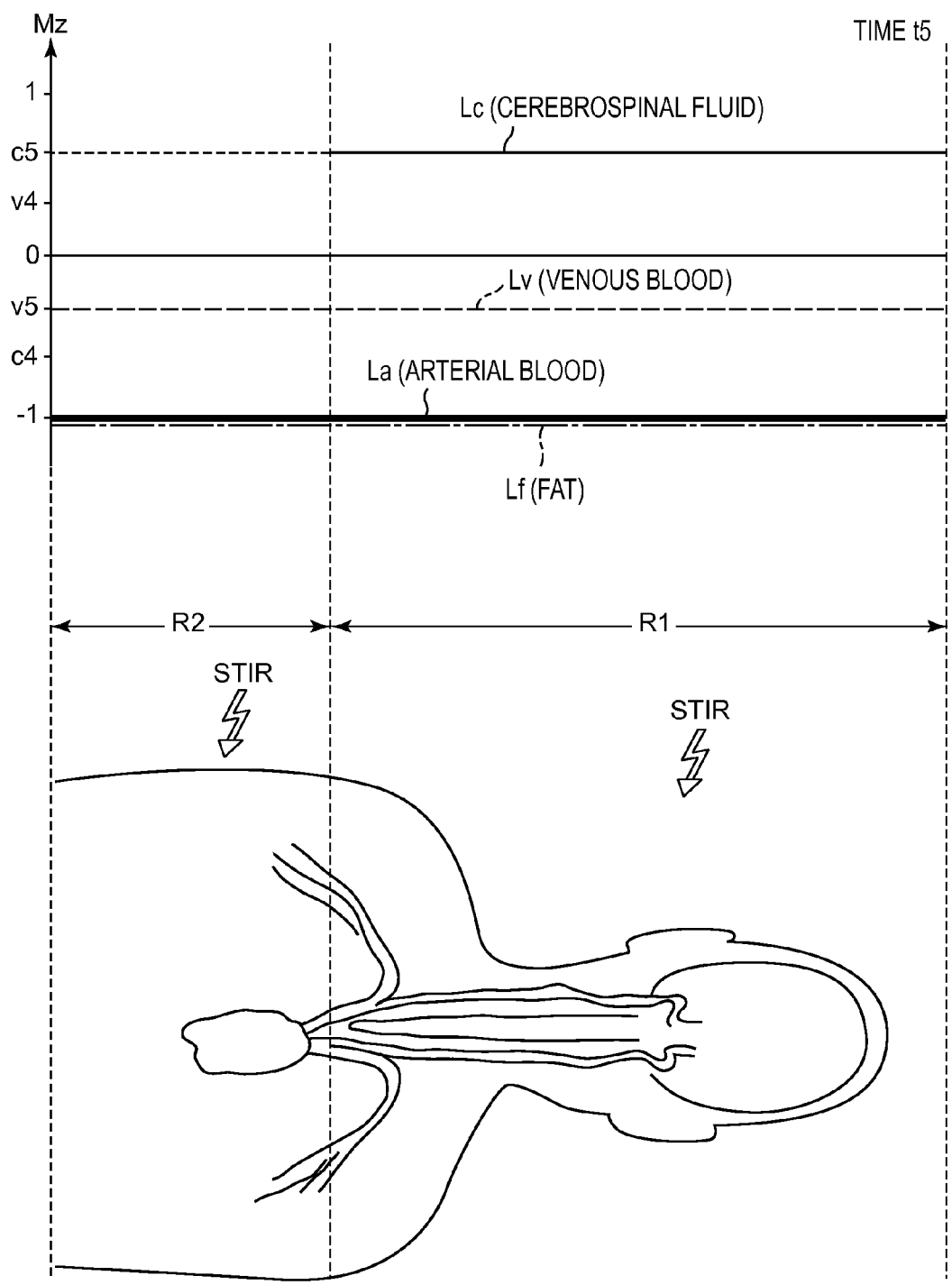
FIG. 8 is a diagram illustrating longitudinal magnetization Mz of arterial blood, cerebrospinal fluid, fat and venous blood lying within the imaging surface at a time t5.

FIG. 8 is a diagram showing the longitudinal magnetization Mz of arterial blood, cerebrospinal fluid, fat and venous blood lying within the imaging surface at the time t5.

A description will be made below of how the longitudinal magnetization Mz of each of arterial blood and background tissues (cerebrospinal fluid, fat and venous blood) changes with the transmission of the fat suppression pulse STIR while referring to FIG. 8.

(i) Longitudinal Magnetization Mz of Arterial Blood

The fat suppression pulse STIR is of a non-selective pulse for inverting the longitudinal magnetization of respective tissues in the entirety of the regions R1 and R2. Thus, the longitudinal magnetization Mz of arterial blood in the regions R1 and R2 are inverted from Mz=1 to Mz=−1 by the transmission of the fat suppression pulse STIR as shown in FIG. 8 (refer to the longitudinal magnetization recovery curve Az of FIG. 4C).

(ii) Longitudinal Magnetization Mz of Background Tissues (Cerebrospinal Fluid, Fat and Venous Blood)

The longitudinal magnetization Mz of cerebrospinal fluid, fat and venous blood are also inverted by the fat suppression pulse STIR. The longitudinal magnetization Mz of cerebrospinal fluid in the region R1 is inverted from Mz=c4 to Mz=c5 as shown in FIG. 8 (refer to the longitudinal magnetization recovery curve Cz of FIG. 4C).

The longitudinal magnetization Mz of fat in each of the regions R1 and R2 is inverted from Mz=1 to Mz=−1 as shown in FIG. 8 (refer to the longitudinal magnetization recovery curve Fz of FIG. 4C).

The longitudinal magnetization Mz of venous blood in each of the regions R1 and R2 is inverted from Mz=v4 to Mz=v5 as shown in FIG. 8 (refer to the longitudinal magnetization recovery curve Vz of FIG. 4C).

(5) Times t5 to t6

After the fat suppression pulse STIR has been transmitted at the time t5, the acquisition of magnetic resonance signals is started at the time t7. A waiting time W2 (=TIb) is however provided between the times t5 and t7 (refer to FIG. 4B). Thus, longitudinal relaxation proceeds during the waiting time W2, and the longitudinal magnetization Mz of each tissue is represented in the following manner at the time t6 lying immediately before the start of the acquisition of the magnetic resonance signals.

Figure 9:
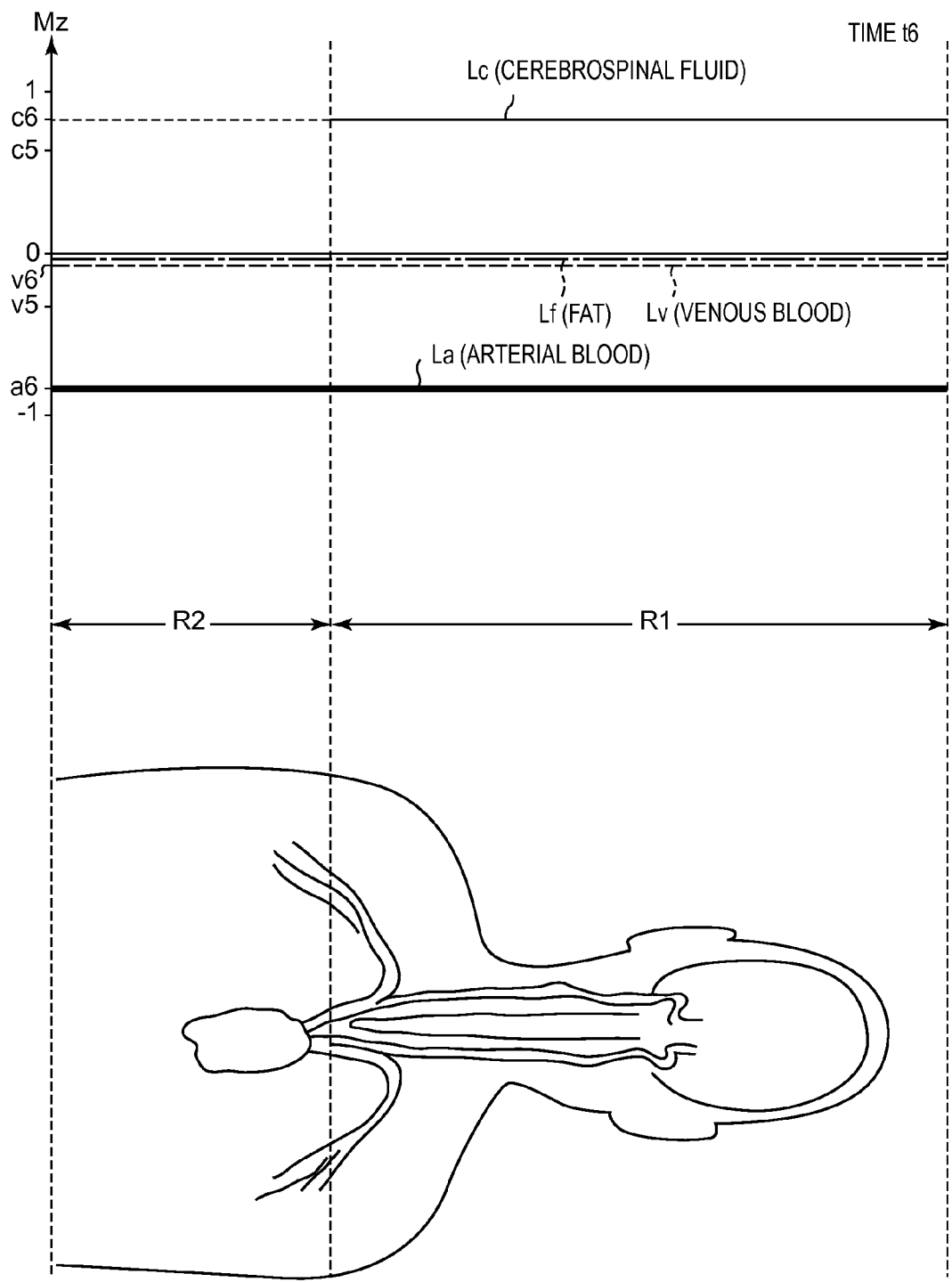
FIG. 9 is a diagram showing longitudinal magnetization Mz of arterial blood, cerebrospinal fluid, fat and venous blood lying within the imaging surface at a time t6.

FIG. 9 is a diagram showing the longitudinal magnetization Mz of arterial blood, cerebrospinal fluid, fat and venous blood lying within the imaging surface at the time t6.

A description will be made below of how the longitudinal magnetization Mz of each of arterial blood and background tissues (cerebrospinal fluid, fat and venous blood) changes during the waiting time W2 while referring to FIG. 9.

(i) Longitudinal Magnetization Mz of Arterial Blood

While the longitudinal magnetization Mz of arterial blood in each of the regions R1 and R2 is Mz=−1 at the time t5 (refer to FIG. 8), the longitudinal magnetization Mz is recovered up to Mz=a6 between the times t5 and t6 as shown in FIG. 9 (refer to the longitudinal magnetization recovery curve Az of FIG. 4C).

(ii) Longitudinal Magnetization Mz of Background Tissues (Cerebrospinal Fluid, Fat and Venous Blood)

The waiting time W2 is set in such a manner that the longitudinal magnetization Mz of fat is recovered from Mz=−1 to Mz=0 (null point). Thus, the longitudinal magnetization Mz of fat in each of the regions R1 and R2 becomes Mz≈0 at the time t6 as shown in FIG. 9 (refer to the longitudinal magnetization recovery curve Fz of FIG. 4C).

The venous blood in each of the regions R1 and R2 is recovered from Mz=v5 to Mz=v6 by the waiting time W2 (refer to the longitudinal magnetization recovery curve Vz of FIG. 4C). Mz=v6 is a value close to the null point.

The longitudinal magnetization Mz of cerebrospinal fluid in the region R1 is recovered from Mz=c5 to Mz=c6 (refer to the longitudinal magnetization recovery curve Cz of FIG. 4C).

(6) Times t7 to t8

A signal acquisition sequence DAQ for acquiring magnetic resonance signals is executed between the times t7 and t8. While the signal acquisition sequence DAQ is being executed, the receiving coil 5 (refer to FIG. 1) receives an MR signal. The received MR signal is transmitted to the signal processing device 62 (refer to FIG. 1), where an image reconstruction is performed. The reconstructed image is displayed on the display device 8 (refer to FIG. 1). Incidentally, the longitudinal magnetization Mz and transverse magnetization Mx of arterial blood and background tissues (cerebrospinal fluid, fat and venous blood) change in the following manner by the execution of the signal acquisition sequence DAQ.

(i) Longitudinal Magnetization Mz

In the present embodiment, the signal acquisition sequence DAQ is a sequence using a 3D FSE method. In the 3D FSE method, a 180° pulse is repeatedly transmitted after the transmission of a 90° pulse. Thus, the longitudinal magnetization Mz of each of arterial blood and background tissues (cerebrospinal fluid, fat and venous blood) becomes a value close to Mz=0 (null point) between the times t7 and t8.

(ii) Transverse Magnetization Mx

As described above, the 90° pulse is first transmitted in the signal acquisition sequence DAQ. With the transmission of the 90° pulse, the longitudinal magnetization Mz=a6 (refer to FIG. 4C) of arterial blood at the time t6 lying immediately before the start of signal acquisition becomes transverse magnetization Mx=a7 at the signal acquisition start time t7 (refer to FIG. 4D). Thereafter, transverse relaxation proceeds and the transverse magnetization Mx of arterial blood becomes Mx=a8 at the signal acquisition end time t8 (refer to the transverse magnetization curve Ax).

The longitudinal magnetization Mz=c6 (refer to FIG. 4C) of cerebrospinal fluid at the time t6 lying immediately before the signal acquisition start becomes transverse magnetization Mx=c7 at the signal acquisition start time t7 (refer to FIG. 4D). Thereafter, transverse relaxation proceeds and the transverse magnetization Mx of cerebrospinal fluid becomes Mx=c8 at the signal acquisition end time t8 (refer to the transverse magnetization curve Cx).

Since the longitudinal magnetization Mz of fat at the time t6 lying immediately before the start of signal acquisition is Mz≈0 (refer to FIG. 4C), the transverse magnetization Mx of fat at the signal acquisition start time t7 is Mx≈0 (refer to FIG. 4D). Thus, the transverse magnetization Mx of fat is Mx≈0 even at the signal acquisition end time t8 (refer to the transverse magnetization curve Fx).

The longitudinal magnetization Mz=v6 (refer to FIG. 4C) of venous blood at the time t6 lying immediately before the start of signal acquisition becomes transverse magnetization Mx=v7 at the signal acquisition start time t7 (refer to FIG. 4D). Since the longitudinal magnetization Mz=v6 of venous blood is a value close to Mz=0, the transverse magnetization Mx=v7 also becomes a value close to Mx=0. Thus, the transverse magnetization Mx of venous blood becomes Mx≈0 at the signal acquisition end time t8 (refer to the transverse magnetization curve Vx).

Figure 10:
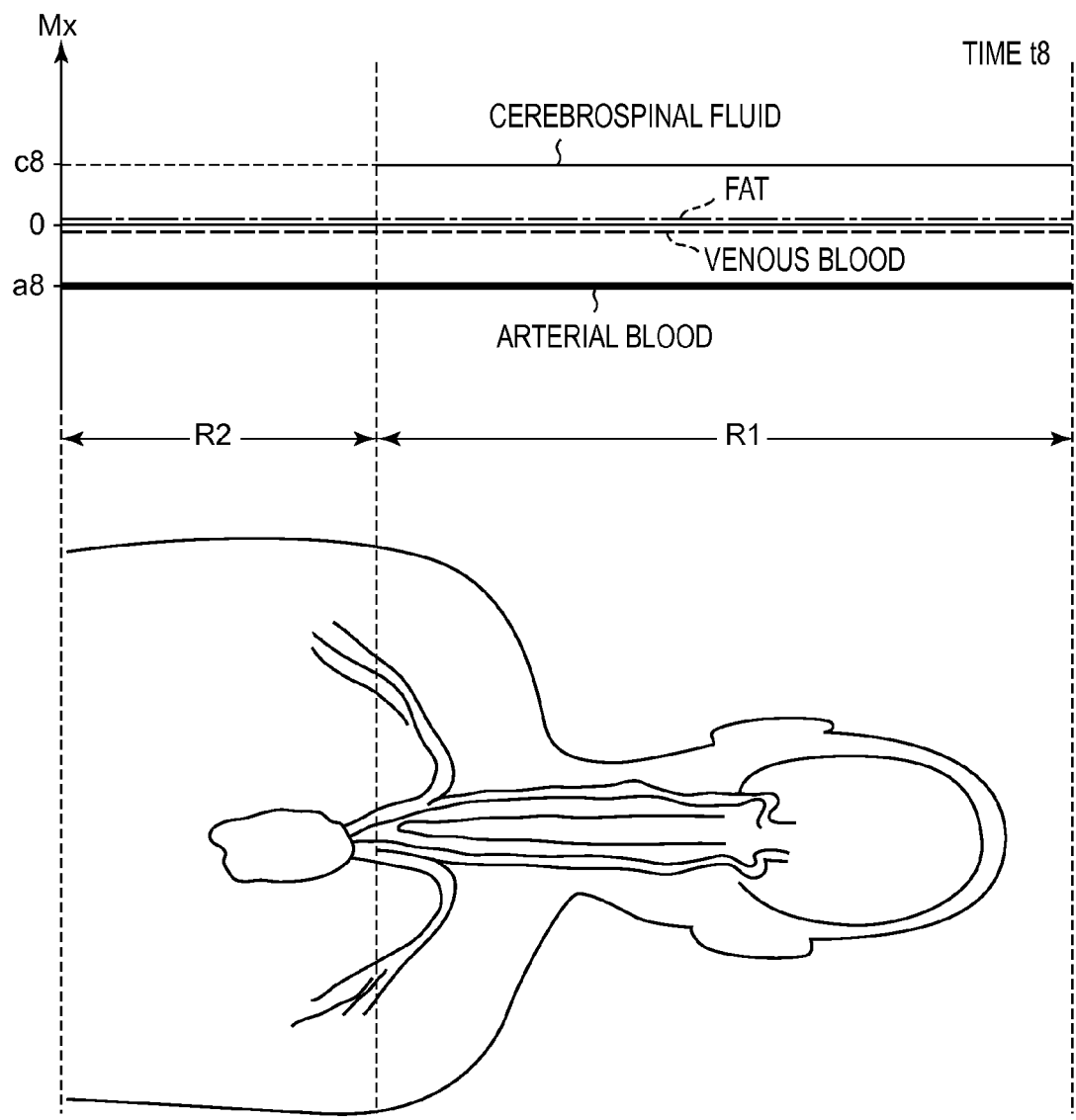
FIG. 10 is a diagram showing transverse and longitudinal magnetization Mx of arterial blood, cerebrospinal fluid, fat and venous blood lying within the imaging surface at a signal acquisition end time t8.

FIG. 10 is a diagram showing transverse and longitudinal magnetization Mx of arterial blood, cerebrospinal fluid, fat and venous blood lying within the imaging surface at the signal acquisition end time t8.

It is understood that referring to FIG. 10, the transverse magnetization Mx of cerebrospinal fluid has a value larger than the transverse magnetization Mx of each of fat and venous blood within the background tissues.

(7) Time t9

In the present embodiment, the pulse sequence does not proceed to the waiting time W3 immediately after the acquisition of the magnetic resonance signals, and −90° x pulse (time t9) and a 180° pulse (time t10) are transmitted before the waiting time W3.

Figure 11:
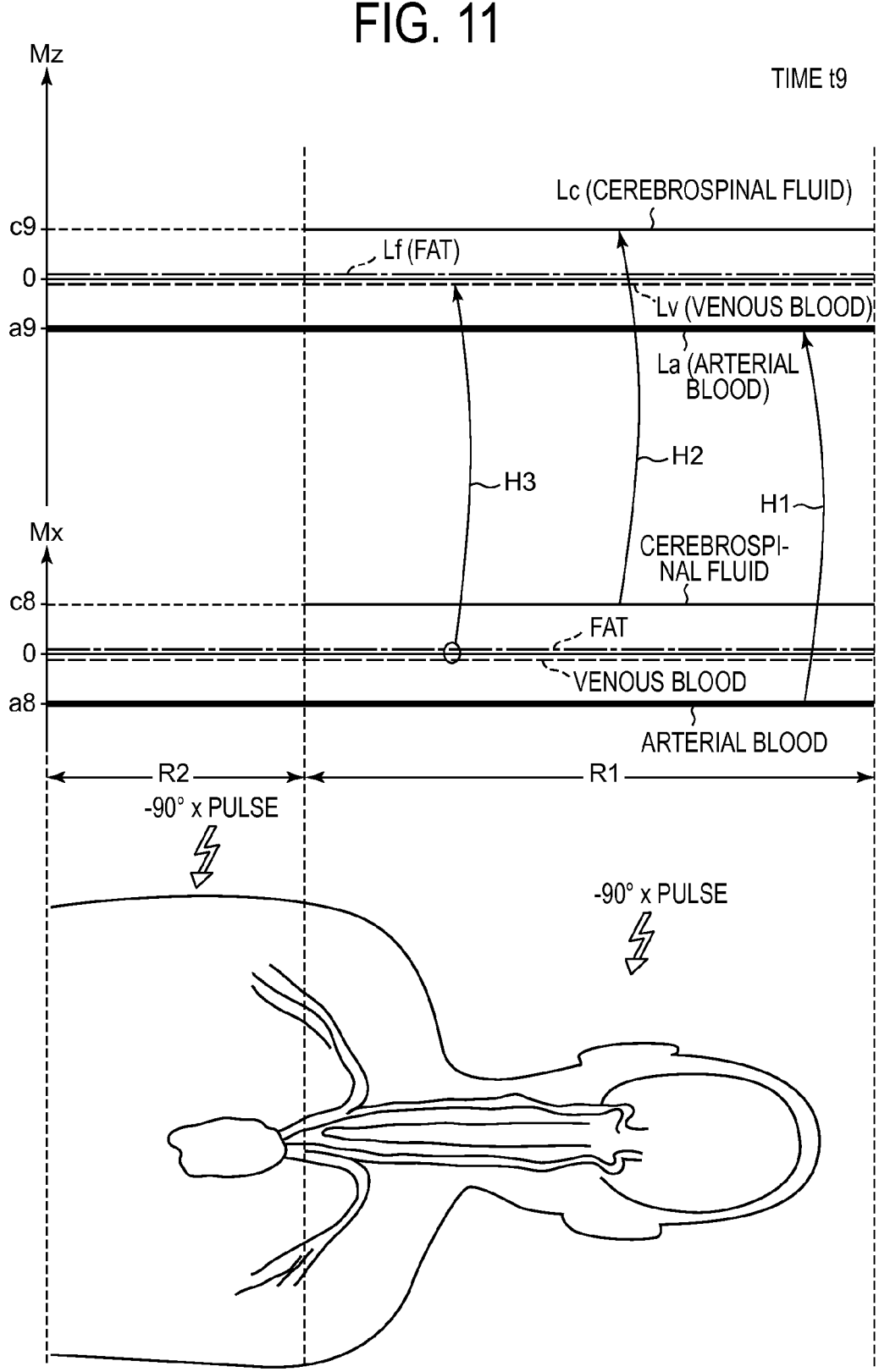
FIG. 11 is a diagram for describing how the magnetization of arterial blood, cerebrospinal fluid, fat and venous blood lying within the imaging surface change according to a −90° x pulse (time t9).

FIG. 11 is a diagram for describing how the magnetization of arterial blood, cerebrospinal fluid, fat and venous blood lying within the imaging surface change according to the −90° x pulse (time t9).

A graph indicative of longitudinal magnetization Mz is shown on the top of FIG. 11, and a graph indicative of transverse magnetization Mx is shown therebelow.

The −90° x pulse is a non-selective pulse for flipping the transverse magnetization Mx to the longitudinal magnetization Mz. Thus, the transverse magnetization Mx=a8 of arterial blood in each of the regions R1 and R2 is flipped to longitudinal magnetization Mz=a9 by the transmission of the −90° x pulse (refer to arrow H1). The transverse magnetization Mx=c8 of cerebrospinal fluid is flipped to longitudinal magnetization Mz=c9 by the transmission of the −90° x pulse (refer to arrow H2). Since the transverse magnetization Mx of each of fat and venous blood is Mx≈0, the transverse magnetization Mx is flipped to longitudinal magnetization Mz≈0 (refer to arrow H3).

Even in FIGS. 4C and 4D, the manner in which the transverse magnetization Mx=a8 of arterial blood is flipped to the longitudinal magnetization Mz=a9 is indicated by the arrow H1, and the manner in which the transverse magnetization Mx=c8 of cerebrospinal fluid is flipped to the longitudinal magnetization Mz=c9 is indicated by the arrow H2. Further, the manner in which the transverse magnetization Mx≈0 of each of fat and venous blood is flipped to the longitudinal magnetization Mz≈0 is indicated by the arrow H3.

(8) Time t10

The 180° pulse for inverting the longitudinal magnetization Mz is transmitted at the time t10 lying immediately after the transmission of the −90° x pulse. With transmission of the 180° pulse, the longitudinal magnetization Mz of each of arterial blood and background tissues (cerebrospinal fluid, fat and venous blood) changes in the following manner (refer to FIG. 12).

Figure 12:
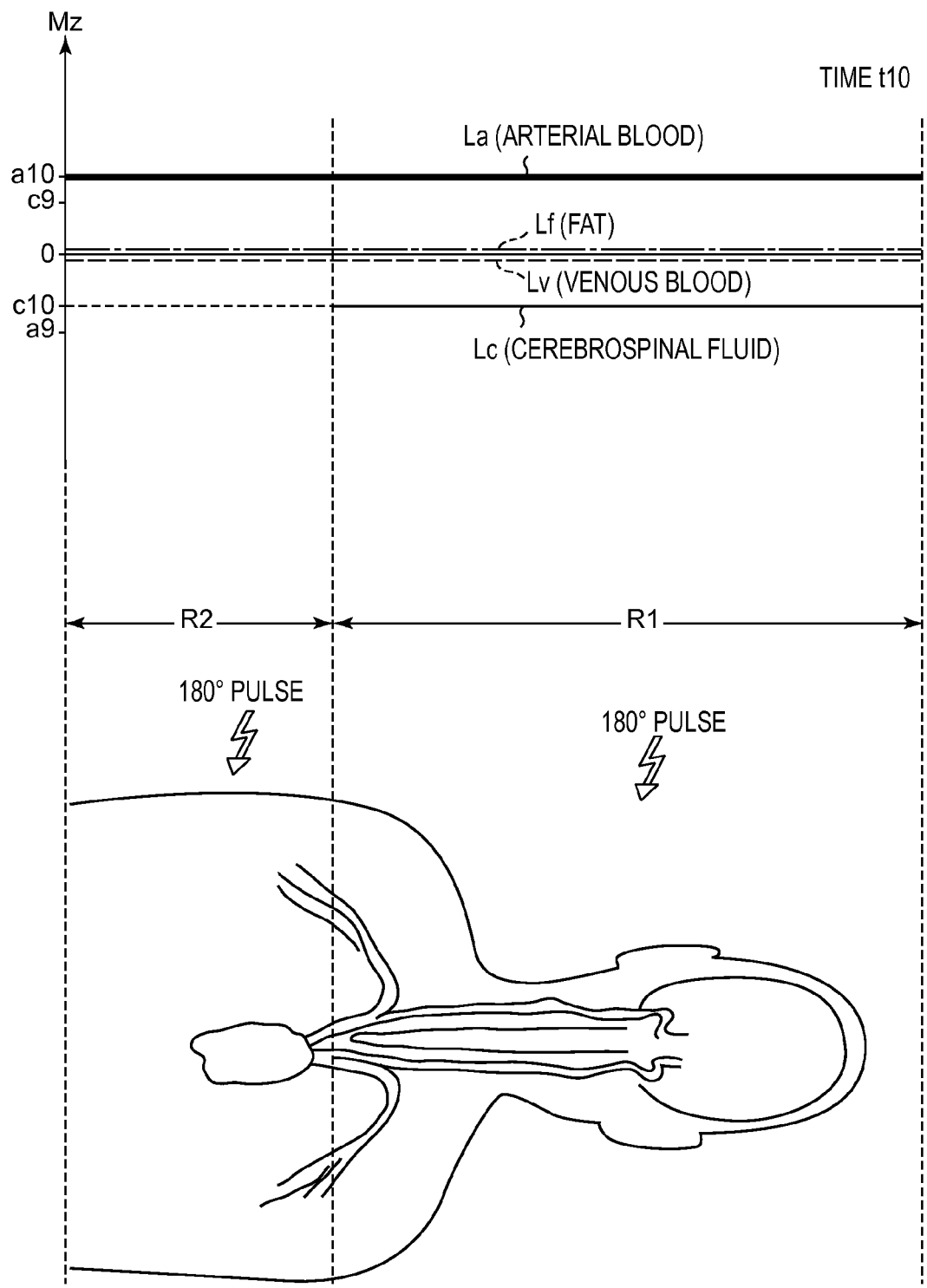
FIG. 12 is a diagram showing longitudinal magnetization Mz of arterial blood, cerebrospinal fluid, fat and venous blood lying within the imaging surface at a time t10.

FIG. 12 is a diagram showing the longitudinal magnetization Mz of arterial blood, cerebrospinal fluid, fat and venous blood lying within the imaging surface at the time t10.

A description will be made below of how the longitudinal magnetization Mz of each of arterial blood and background tissues (cerebrospinal fluid, fat and venous blood) changes by the transmission of a 180° pulse while referring to FIG. 12.

(i) Longitudinal Magnetization Mz of Arterial Blood

The 180° pulse is of a non-selective pulse for inverting the longitudinal magnetization of the entire imaging surface. Thus, the longitudinal magnetization Mz of arterial blood in each of the regions R1 and R2 is inverted from Mz=a9 to Mz=a10 at the time t10 as shown in FIG. 12 (refer to the longitudinal magnetization recovery curve Az of FIG. 4C).

(ii) Longitudinal Magnetization Mz of Background Tissues (Cerebrospinal Fluid, Fat and Venous Blood)

The longitudinal magnetization Mz of cerebrospinal fluid in the region R1 is inverted from Mz=c9 to Mz=c10 by the transmission of the 180° pulse as shown in FIG. 12 (refer to the longitudinal magnetization recovery curve Cz of FIG. 4C).

Incidentally, since the longitudinal magnetization Mx of each of fat and venous blood is Mx≈0 at the time t9 (refer to FIG. 1), the longitudinal magnetization is Mz≈0 even at the time t10.

With the transmission of the 180° pulse at the time t10, the first pulse sequence PS is completed. Incidentally, while the longitudinal magnetization Mz of each of fat and venous blood at the time t6 lying immediately before the signal acquisition is a value close to Mz=0 in the first pulse sequence PS as shown in FIG. 4, the longitudinal magnetization Mz of cerebrospinal fluid large in T1 value has a relatively large positive value (Mz=c6). With the further repetitive execution of the pulse sequence PS, however, the longitudinal magnetization Mz of cerebrospinal fluid large in T1 value can also be made close to a null point at the time immediately before the signal acquisition. A description will hereinafter be made of how the magnetization of arterial blood and background tissues (cerebrospinal fluid, fat and venous blood) change by further executing the pulse sequence PS repeatedly.

After the completion of the first pulse sequence PS, the coil control device 61 detects two R waves RW3 and RW4 (times t11 and t12). After the second R wave RW4 has been detected by the coil control device 61, the coil control device 61 controls the gradient coil and the transmitting coil in synchronization with the R wave RW4 in such a manner that the second pulse sequence PS is started. Thus, a waiting time W3 is provided between the first pulse sequence PS and the second pulse sequence PS. A description will next be made of how the magnetization of each tissue changes till the completion of the second pulse sequence PS after the completion of the first pulse sequence PS with the waiting time W3 interposed therebetween.

FIGS. 13A-13D are diagrams for describing how the magnetization of each tissue changes from the end of a first pulse sequence PS to the end of a second pulse sequence PS with a waiting time W3 interposed therebetween.

Longitudinal magnetization recovery curves Az, Cz, Fz and Vz and transverse magnetization recovery curves Ax, Cx, Fx and Vx will be explained below for every t10, . . . , t21 of times.

(1) Times t10 to t13

A waiting time W3 (refer to FIG. 13B) is provided till the start of the second pulse sequence PS after a 180° pulse has been transmitted at the time t10. Thus, longitudinal relaxation proceeds during the waiting time W3. At the time t13 lying immediately before a selective inversion pulse SIR in the second pulse sequence PS is transmitted, the longitudinal magnetization Mz of each tissue changes in the following manner.

Figure 14:
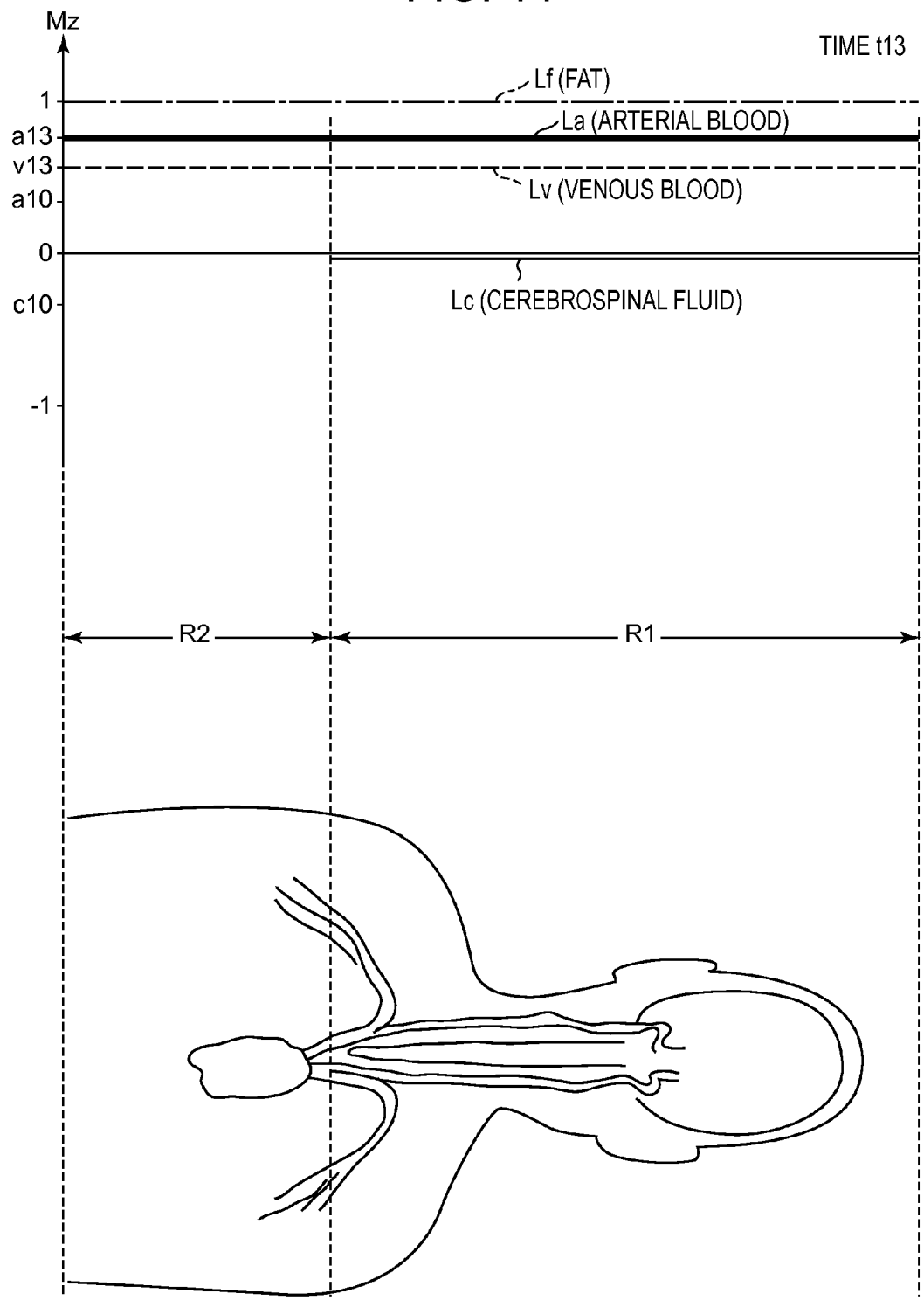
FIG. 14 is a diagram showing longitudinal magnetization Mz of arterial blood, cerebrospinal fluid, fat and venous blood lying within the imaging surface at a time t13.

FIG. 14 is a diagram showing the longitudinal magnetization Mz of arterial blood, cerebrospinal fluid, fat and venous blood lying within the imaging surface at the time t13.

A description will hereinafter be made of how the longitudinal magnetization Mz of arterial blood and background tissues (cerebrospinal fluid, fat and venous blood) change during the waiting time W3 while referring to FIG. 14.

(i) Longitudinal Magnetization Mz of Arterial Blood

While the longitudinal magnetization Mz of arterial blood in the region R2 is Mz=a10 at the time t10, the longitudinal magnetization Mz is recovered to Mz=a13 during the waiting time W3.

The arterial blood in the region R2 flows into the region R1 during the waiting time W3. Since the longitudinal magnetization Mz of arterial blood in the region R2 is Mz=a13 at the time t13, the arterial blood in the region R2 flows into the region R1, so that the arterial blood in the region R1 as well as the arterial blood in the region R2 becomes Mz=a13 at the time t13.

(ii) Longitudinal Magnetization Mz of Background Tissues (Cerebrospinal Fluid, Fat and Venous Blood)

The waiting time W3 is set in such a manner that the longitudinal magnetization Mz of cerebrospinal fluid is recovered from Mz=c10 to Mz=0 (null point). The longitudinal magnetization Mz of cerebrospinal fluid in each of the regions R1 and R2 is Mz=c10 at the time t10 (refer to FIG. 12). Thus, the longitudinal magnetization Mz of cerebrospinal fluid reaches from Mz=c10 to Mz≈0 during the waiting time W3 as shown in FIG. 13 (refer to the longitudinal magnetization recovery curve Cz of FIG. 13C.

Figure 13:
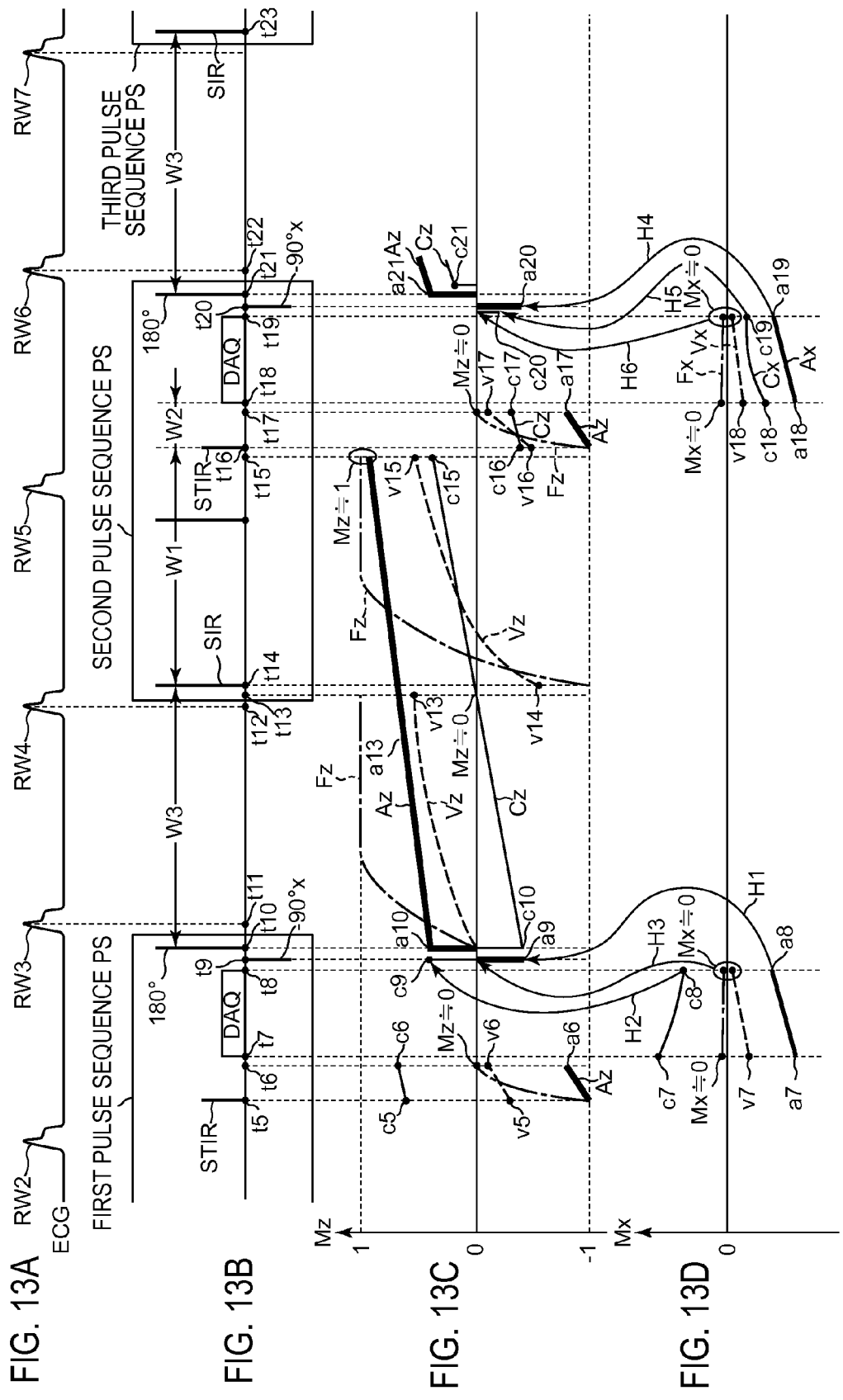
FIGS. 13A, 13B, 13C, and 13D are diagrams for describing how the magnetization of each tissue changes from the end of a first pulse sequence PS to the end of a second pulse sequence PS with a waiting time W3 interposed therebetween.

Since the fat is small in T1 value, the longitudinal magnetization Mz of fat is recovered from Mz≈0 to Mz=1 at the time t13 as shown in FIG. 13 (refer to the longitudinal magnetization recovery curve Fz of FIG. 13C.

Since the venous blood has a T1 value corresponding to a value between those for the fat and cerebrospinal fluid, the longitudinal magnetization thereof is recovered from Mz≈0 to Mz=v13 at the time t13 (refer to the longitudinal magnetization recovery curve Vz of FIG. 13C).

(2) Time t14

A selective inversion pulse SIR (refer to FIG. 13B) in the second pulse sequence PS is transmitted at the time t14. With the transmission of the selective inversion pulse SIR, the longitudinal magnetization Mz of each of arterial blood and background tissues (cerebrospinal fluid, fat and venous blood) changes as follows (refer to FIG. 15).

Figure 15:
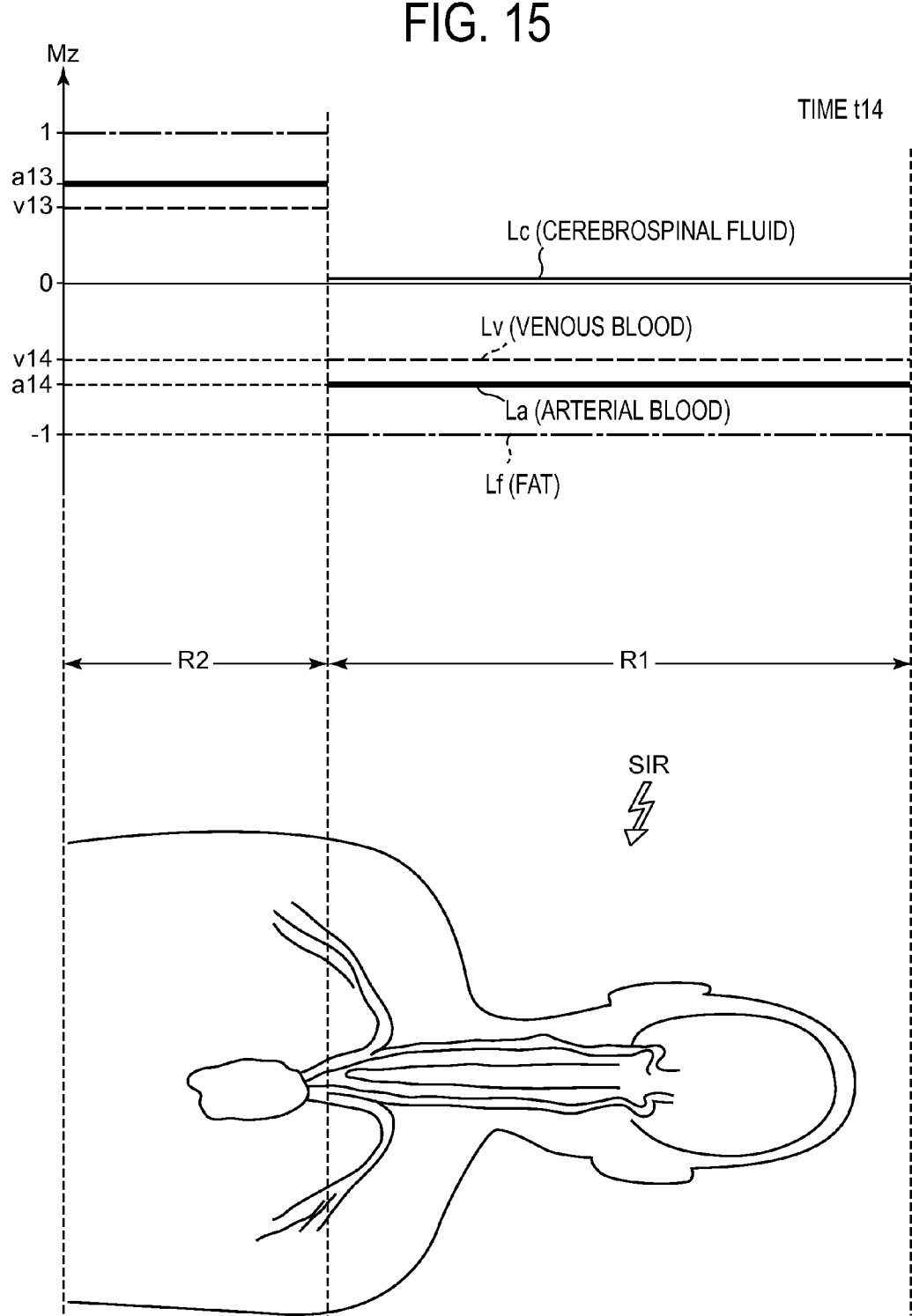
FIG. 15 is a diagram showing longitudinal magnetization Mz of arterial blood, cerebrospinal fluid, fat and venous blood lying within the imaging surface at a time t14.

FIG. 15 is a diagram showing the longitudinal magnetization Mz of arterial blood, cerebrospinal fluid, fat and venous blood lying within the imaging surface at the time t14.

A description will hereinafter be made of how the behaviors of longitudinal magnetization Mz of arterial blood and background tissues (cerebrospinal fluid, fat and venous blood) change by the transmission of the selective inversion pulse SIR while referring to FIG. 15.

(i) Longitudinal Magnetization Mz of Arterial Blood

The selective inversion pulse SIR is of a selective pulse for inverting the longitudinal magnetization of each tissue lying in the region R1 and avoiding the inversion of the longitudinal magnetization of each tissue lying in the region R2. Thus, the longitudinal magnetization Mz of arterial blood in the region R1 is inverted from Mz=a13 to Mz=a14 as shown in FIG. 15 by the transmission of the selective inversion pulse SIR.

On the other hand, since the longitudinal magnetization Mz of arterial blood in the region R2 is not affected by the selective inversion pulse SIR, the longitudinal magnetization Mz remains at Mz=a13 even at the time t14 as shown in FIG. 15 (incidentally, since the time interval between the times t13 and t14 is extremely short, the amount of recovery of the longitudinal magnetization Mz between the times t13 and t14 is ignored). The longitudinal magnetization recovery curve Az shown in FIG. 13C concretely shows the manner in which the longitudinal magnetization Mz of arterial blood in the region R2 remains at Mz=a13 without being affected by the selective inversion pulse SIR (incidentally, the manner in which the longitudinal magnetization Mz of arterial blood in the region R1 is inverted from Mz=a13 to Mz=a14, is not shown in FIG. 13C).

(ii) Longitudinal Magnetization Mz of Background Tissues (Cerebrospinal Fluid, Fat and Venous Blood)

The longitudinal magnetization Mz of cerebrospinal fluid in the region R1 is Mz≈0 at the time t13 lying immediately before the transmission of the selective inversion pulse SIR (refer to FIG. 13C). Accordingly, the longitudinal magnetization Mz of cerebrospinal fluid in the region R1 is Mz≈0 as shown in FIG. 15 even though the selective inversion pulse SIR is transmitted (refer to the longitudinal magnetization recovery curve Cz of FIG. 13C).

The longitudinal magnetization Mz of fat in each of the regions R1 and R2 is Mz=1 at the time t13 immediately before the transmission of the selective inversion pulse SIR (refer to FIG. 13C). Thus, the longitudinal magnetization Mz of fat in the region R1 is inverted from Mz=1 to Mz=−1 by the transmission of the selective inversion pulse SIR as shown in FIG. 15 (refer to the longitudinal magnetization recovery curve Fz of FIG. 13C). Since, however, the longitudinal magnetization Mz of fat in the region R2 is not affected by the selective inversion pulse SIR, the longitudinal magnetization Mz remains at Mz=1.

The longitudinal magnetization Mz of venous blood in each of the regions R1 and R2 is Mz=v13 at the time t13 lying immediately before the transmission of the selective inversion pulse SIR (refer to FIG. 13C). Thus, the longitudinal magnetization Mz of venous blood in the region R1 is inverted from Mz=v13 to Mz=v14 by the transmission of the selective inversion pulse SIR as shown in FIG. 15 (refer to the longitudinal magnetization recovery curve Vz of FIG. 13C). Since, however, the longitudinal magnetization Mz of venous blood in the region R2 is not affected by the selective inversion pulse SIR, the longitudinal magnetization Mz remains at Mz=v13.

(3) Times t14 to t15

After the selective inversion pulse SIR has been transmitted at the time t14, a fat suppression pulse STIR is transmitted at the time t16. A waiting time W1 is however provided between the times t14 and t16. Thus, longitudinal relaxation proceeds during the waiting time W1, and the longitudinal magnetization Mz of each tissue is represented in the following manner at the time t15 lying immediately before the transmission of the fat suppression pulse STIR.

Figure 16:
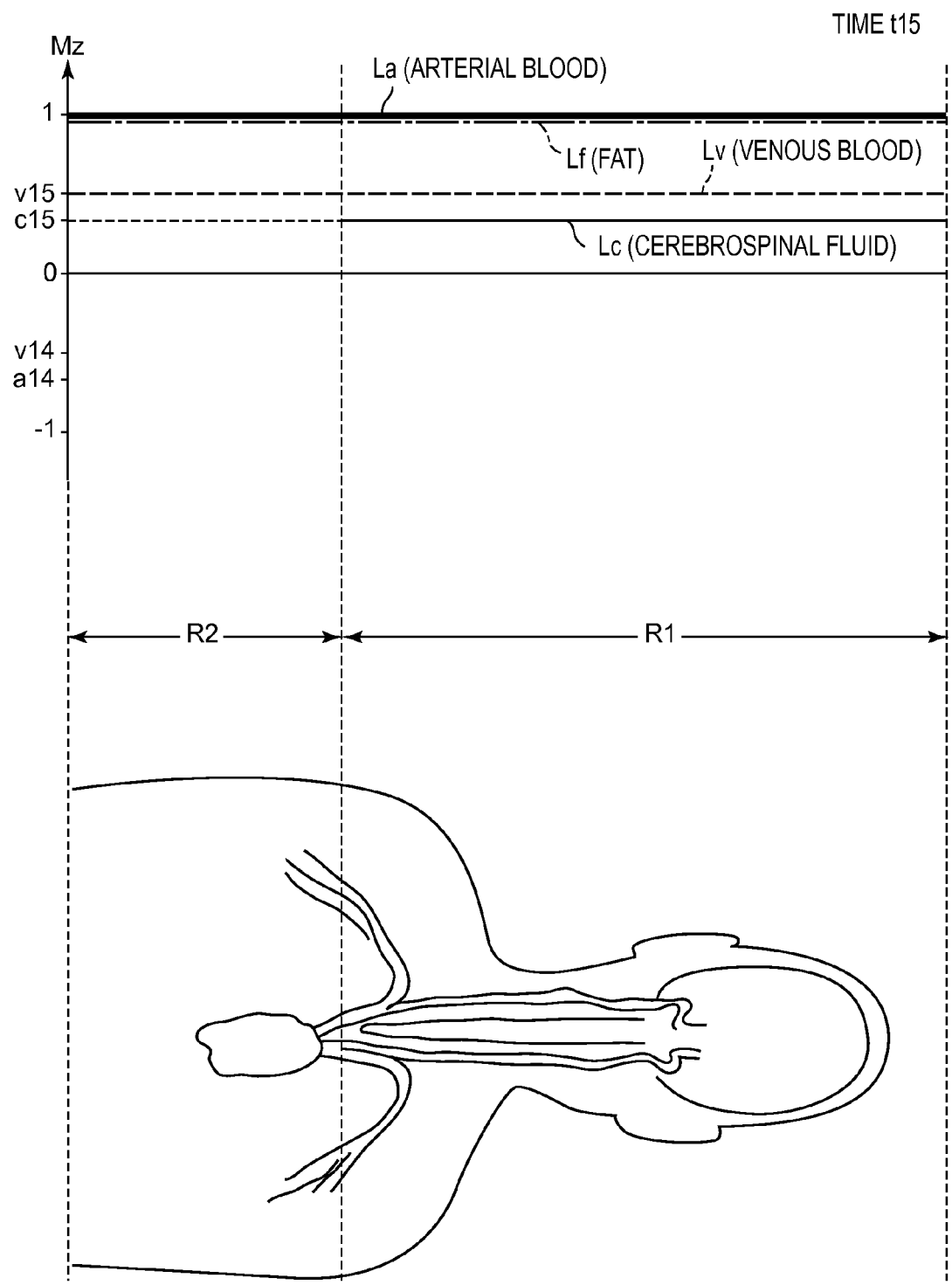
FIG. 16 is a diagram illustrating longitudinal magnetization Mz of arterial blood, cerebrospinal fluid, fat and venous blood lying within the imaging surface at a time t15.

FIG. 16 is a diagram showing the longitudinal magnetization Mz of arterial blood, cerebrospinal fluid, fat and venous blood lying within the imaging surface at the time t15.

A description will be made below of how the longitudinal magnetization Mz of each of arterial blood and background tissues (cerebrospinal fluid, fat and venous blood) changes during the waiting time W1 while referring to FIG. 16.

(i) Longitudinal Magnetization Mz of Arterial Blood

The longitudinal magnetization Mz of arterial blood in the region R2 is Mz=a13 at the time t14 (refer to FIG. 15). However, longitudinal relaxation proceeds during the waiting time W1, and the longitudinal magnetization Mz of arterial blood in the region R2 is recovered to Mz=1 at the time t15 as shown in FIG. 16.

The arterial blood in the region R2 flows into the region R1 during the waiting time W1. Since the longitudinal magnetization Mz of arterial blood in the region R2 is Mz≈1 at the time t15, the arterial blood in the region R2 flows into the region R1, so that the arterial blood in the region R1 as well as the arterial blood in the region R2 becomes Mz=1 at the time t15.

(ii) Longitudinal Magnetization Mz of Background Tissues (Cerebrospinal Fluid, Fat and Venous Blood)

The longitudinal magnetization Mz of cerebrospinal blood in the region R1 is Mz≈0 at the time t14 (refer to FIG. 15). However, the longitudinal magnetization is gradually recovered during the waiting time W1, and the longitudinal magnetization Mz of cerebrospinal fluid in the region R1 is recovered to Mz=c15 at the time t15 as shown in FIG. 16 (refer to the longitudinal magnetization recovery curve Cz of FIG. 13C).

The longitudinal magnetization Mz of fat in the region R1 is Mz=−1 at the time t14 (refer to FIG. 15). Since, however, the fat is small in T1 value, the longitudinal magnetization Mz of fat in the region R1 is recovered to Mz=1 at the time t15 (refer to the longitudinal magnetization recovery curve Fz of FIG. 13C). Incidentally, since the longitudinal magnetization Mz of fat in the region R2 is MZ=1 at the time t14 (refer to FIG. 15), the longitudinal magnetization Mz remains at Mz=1 at the time t15.

The venous blood in the region R1 is recovered to Mz=v15 at the time t15 as shown in FIG. 16 (refer to the longitudinal magnetization recovery curve Vz of FIG. 13C). Since the venous blood in the region R1 flows into the region R2 during the waiting time W1, the longitudinal magnetization Mz of venous blood in the region R2 also becomes Mz=v15 at the time t15 as shown in FIG. 16.

(4) Time t16

At the time t16, a fat suppression pulse STIR (refer to FIG. 13B) is transmitted. With the transmission of the fat suppression pulse STIR, the longitudinal magnetization Mz of each of arterial blood and background tissues (cerebrospinal fluid, fat and venous blood) changes in the following manner (refer to FIG. 17).

Figure 17:
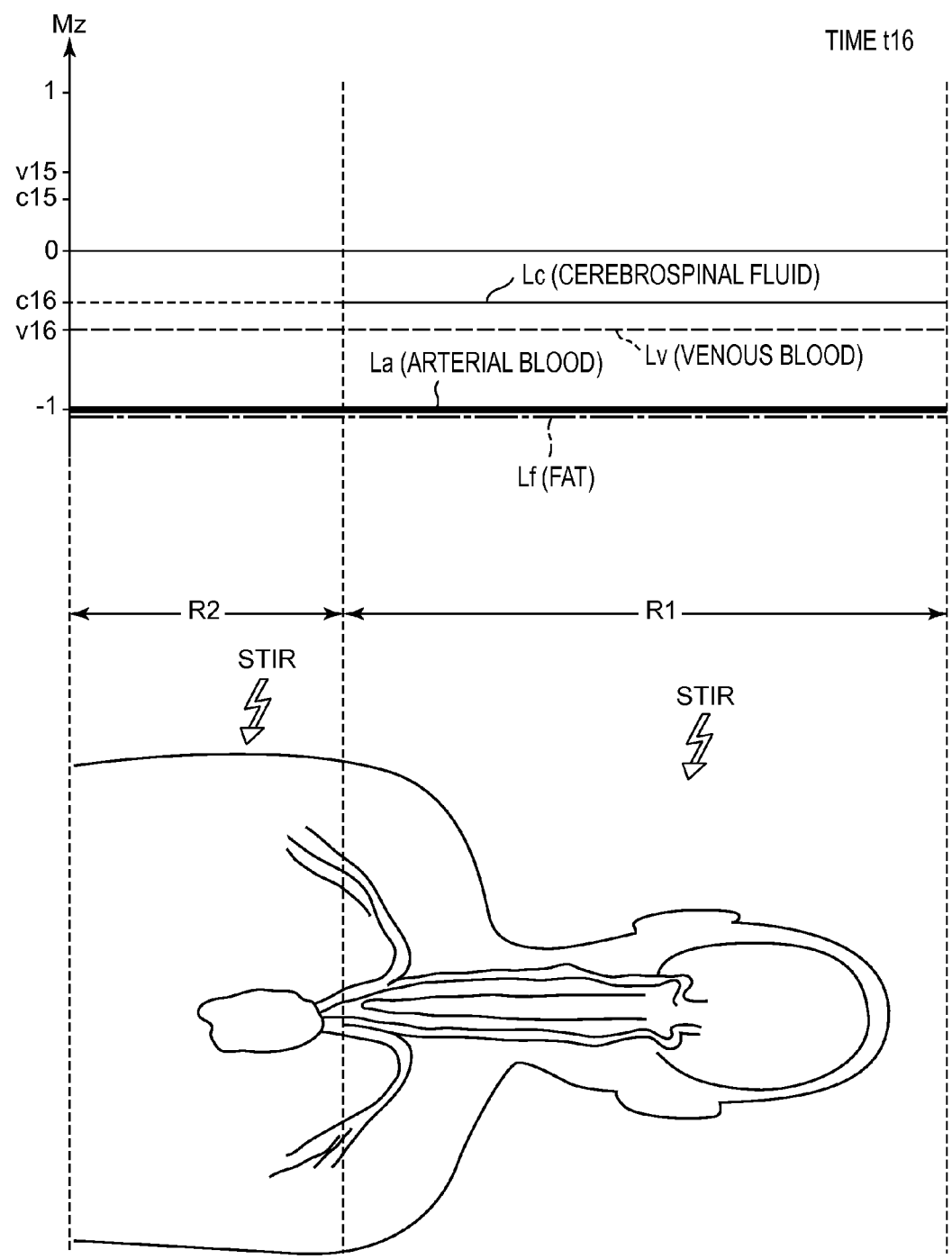
FIG. 17 is a diagram depicting longitudinal magnetization Mz of arterial blood, cerebrospinal fluid, fat and venous blood lying within the imaging surface at a time t16.

FIG. 17 is a diagram showing the longitudinal magnetization Mz of arterial blood, cerebrospinal fluid, fat and venous blood lying within the imaging surface at the time t16.

A description will hereinafter be made of how the longitudinal magnetization Mz of arterial blood and background tissues (cerebrospinal fluid, fat and venous blood) change by the transmission of the fat suppression pulse STIR while referring to FIG. 17.

(i) Longitudinal Magnetization Mz of Arterial Blood

The fat suppression pulse STIR is of a non-selective pulse for inverting the longitudinal magnetization of respective tissues in the entirety of the regions R1 and R2. Thus, the longitudinal magnetization Mz of arterial blood in the regions R1 and R2 are inverted from Mz=1 to Mz=−1 by the transmission of the fat suppression pulse STIR as shown in FIG. 17 (refer to the longitudinal magnetization recovery curve Az of FIG. 13C).

(ii) Longitudinal Magnetization Mz of Background Tissues (Cerebrospinal Fluid, Fat and Venous Blood)

The longitudinal magnetization Mz of cerebrospinal fluid, fat and venous blood are also inverted by the fat suppression pulse STIR. The longitudinal magnetization Mz of cerebrospinal fluid in the region R1 is inverted from Mz=c15 to Mz=c16 as shown in FIG. 17 (refer to the longitudinal magnetization recovery curve Cz of FIG. 13C).

The longitudinal magnetization Mz of fat in each of the regions R1 and R2 is inverted from Mz=1 to Mz=−1 as shown in FIG. 17 (refer to the longitudinal magnetization recovery curve Fz of FIG. 13C).

The longitudinal magnetization Mz of venous blood in each of the regions R1 and R2 is inverted from Mz=v15 to Mz=v16 as shown in FIG. 17 (refer to the longitudinal magnetization recovery curve Vz of FIG. 13C).

(5) Times t16 to t17

After the fat suppression pulse STIR has been transmitted at the time t16, signal acquisition is started at the time t18. A waiting time W2 is however provided between the times t16 and t18 (refer to FIG. 13B). Thus, longitudinal relaxation proceeds during the waiting time W2, and the longitudinal magnetization Mz of each tissue is represented in the following manner at the time t17 lying immediately before the start of the signal acquisition.

Figure 18:
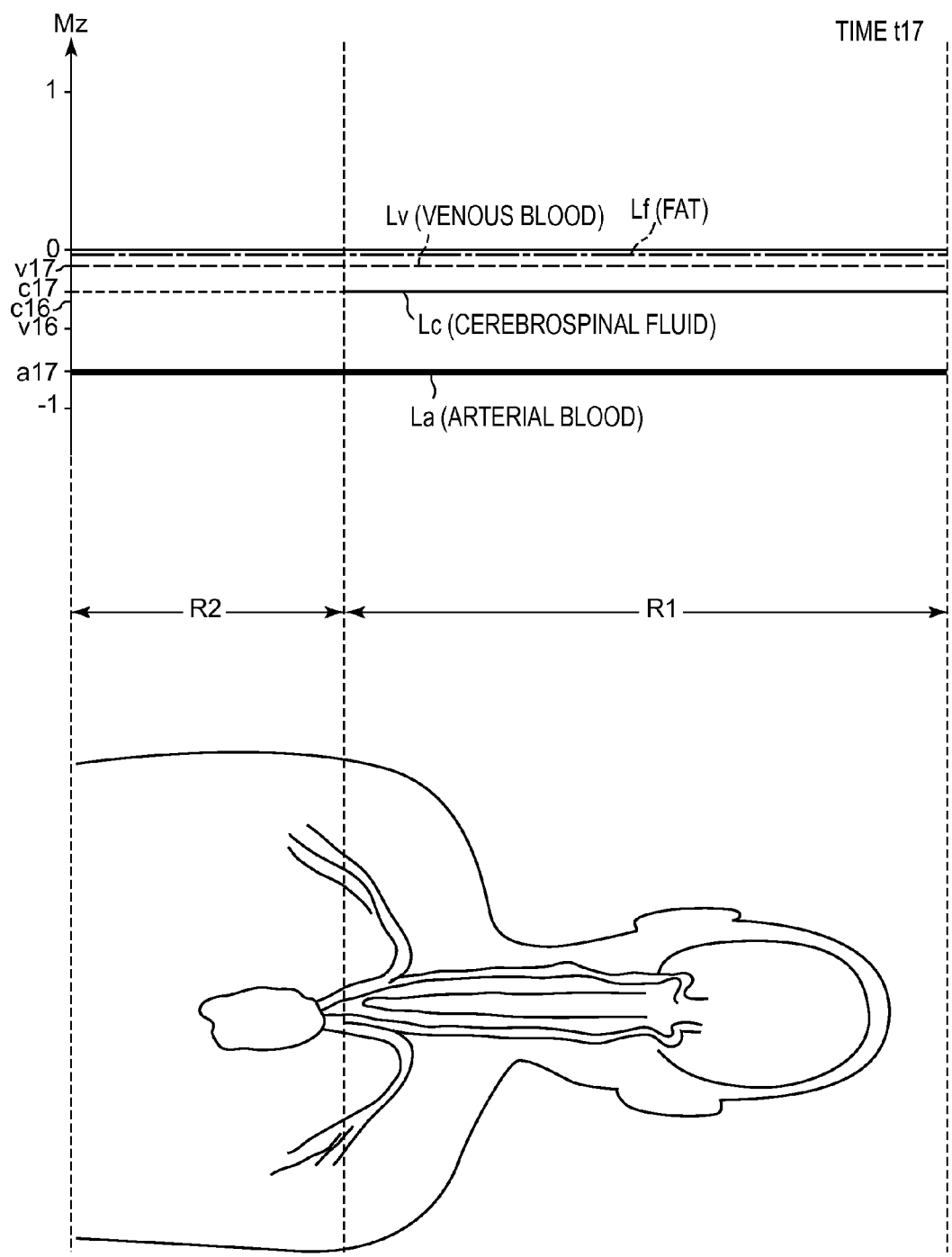
FIG. 18 is a diagram showing longitudinal magnetization Mz of arterial blood, cerebrospinal fluid, fat and venous blood lying within the imaging surface at a time t17.

FIG. 18 is a diagram showing the longitudinal magnetization Mz of arterial blood, cerebrospinal fluid, fat and venous blood lying within the imaging surface at the time t17.

A description will be made below of how the longitudinal magnetization Mz of each of arterial blood and background tissues (cerebrospinal fluid, fat and venous blood) changes during the waiting time W2 while referring to FIG. 18.

(i) Longitudinal Magnetization Mz of Arterial Blood

While the longitudinal magnetization Mz of arterial blood in each of the regions R1 and R2 is Mz=−1 at the time t16 (refer to FIG. 17), the longitudinal magnetization Mz is recovered up to Mz=a6 between the times t16 and t17 as shown in FIG. 18 (refer to the longitudinal magnetization recovery curve Az of FIG. 13C).

(ii) Longitudinal Magnetization Mz of Background Tissues (Cerebrospinal Fluid, Fat and Venous Blood)

The waiting time W2 is set in such a manner that the longitudinal magnetization Mz of fat is recovered from Mz=−1 to Mz=0 (null point). Thus, the longitudinal magnetization Mz of fat in each of the regions R1 and R2 becomes Mz≈0 at the time t17 as shown in FIG. 18 (refer to the longitudinal magnetization recovery curve Fz of FIG. 13C).

The venous blood in each of the regions R1 and R2 is recovered from Mz=v16 to Mz=v17 by the waiting time W2 (refer to the longitudinal magnetization recovery curve Vz of FIG. 13C). Mz=v17 is a value close to the null point.

The longitudinal magnetization Mz of cerebrospinal fluid in the region R1 is recovered from Mz=c16 to Mz=c17 (refer to the longitudinal magnetization recovery curve Cz of FIG. 13C).

(6) Times t18 to t19

A signal acquisition sequence DAQ for acquiring magnetic resonance signals is executed between the times t18 and t19. While the signal acquisition sequence DAQ is being executed, the receiving coil 5 (refer to FIG. 1) receives an MR (Magnetic Resonance) signal. The received MR signal is transmitted to the signal processing device 62 (refer to FIG. 1), where an image reconstruction is performed. The reconstructed image is displayed on the display device 8 (refer to FIG. 1). Incidentally, the longitudinal magnetization Mz and transverse magnetization Mx of arterial blood and background tissues (cerebrospinal fluid, fat and venous blood) change in the following manner by the execution of the signal acquisition sequence DAQ.

(i) Longitudinal Magnetization Mz

In the present embodiment, the signal acquisition sequence DAQ is a sequence using a 3D FSE method. In the 3D FSE method, a 180° pulse is repeatedly transmitted after the transmission of a 90° pulse. Accordingly, the longitudinal magnetization Mz of each of arterial blood and background tissues (cerebrospinal fluid, fat and venous blood) becomes a value close to Mz=0 (null point) between the times t18 and t19.

(ii) Transverse Magnetization Mx

As described above, the 90° pulse is first transmitted in the signal acquisition sequence DAQ. With the transmission of the 90° pulse, the longitudinal magnetization Mz=a17 (refer to FIG. 13C) of arterial blood at the time t17 lying immediately before the start of signal acquisition becomes transverse magnetization Mx=a18 at the signal acquisition start time t18 (refer to FIG. 13D). Thereafter, transverse relaxation proceeds and the transverse magnetization Mx of arterial blood becomes Mx=a19 at the signal acquisition end time t19 (refer to the transverse magnetization curve Ax).

The longitudinal magnetization Mz=c17 (refer to FIG. 13C) of cerebrospinal fluid at the time t17 lying immediately before the signal acquisition start becomes transverse magnetization Mx=c18 at the signal acquisition start time t18 (refer to FIG. 13D). Thereafter, transverse relaxation proceeds and the transverse magnetization Mx of cerebrospinal fluid becomes Mx=c19 at the signal acquisition end time t19 (refer to the transverse magnetization curve Cx).

Since the longitudinal magnetization Mz of fat at the time t17 lying immediately before the start of signal acquisition is Mz=0 (refer to FIG. 13C), the transverse magnetization Mx of fat at the signal acquisition start time t18 is Mx=0 (refer to FIG. 13D). Thus, the transverse magnetization Mx of fat is Mx=0 even at the signal acquisition end time t19 (refer to the transverse magnetization curve Fx).

The longitudinal magnetization Mz=v17 (refer to FIG. 13C) of venous blood at the time t17 lying immediately before the start of signal acquisition becomes transverse magnetization Mx=v18 at the signal acquisition start time t18 (refer to FIG. 13D). Since the longitudinal magnetization Mz=v17 of venous blood is a value close to Mz=0, the transverse magnetization Mx=v18 also becomes a value close to Mx=0. Thus, the transverse magnetization Mx of venous blood becomes Mx=0 at the signal acquisition end time t19 (refer to the transverse magnetization curve Vx).

Figure 19:
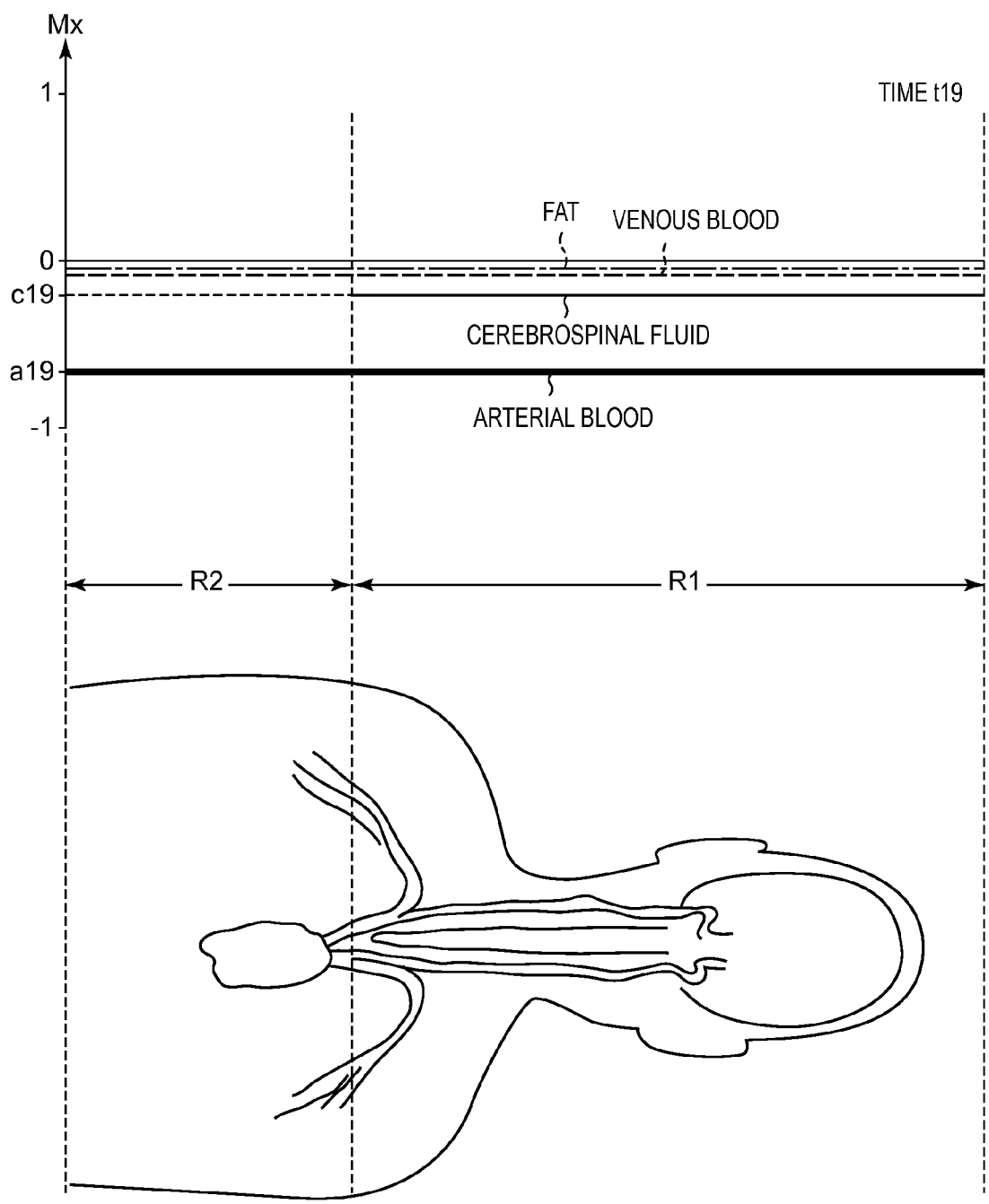
FIG. 19 is a diagram illustrating transverse and longitudinal magnetization Mx of arterial blood, cerebrospinal fluid, fat and venous blood lying within the imaging surface at a signal acquisition end time t19.

FIG. 19 is a diagram showing transverse and longitudinal magnetization Mx of arterial blood, cerebrospinal fluid, fat and venous blood lying within the imaging surface at the signal acquisition end time t19.

It is understood that referring to FIG. 19, the transverse magnetization Mx of cerebrospinal fluid has a value (Mx=c19) slightly larger than the transverse magnetization Mx of each of fat and venous blood within the background tissues.

(7) Time t20

At the time t20 immediately after the signal acquisition, a −90° x pulse is transmitted.

Figure 20:
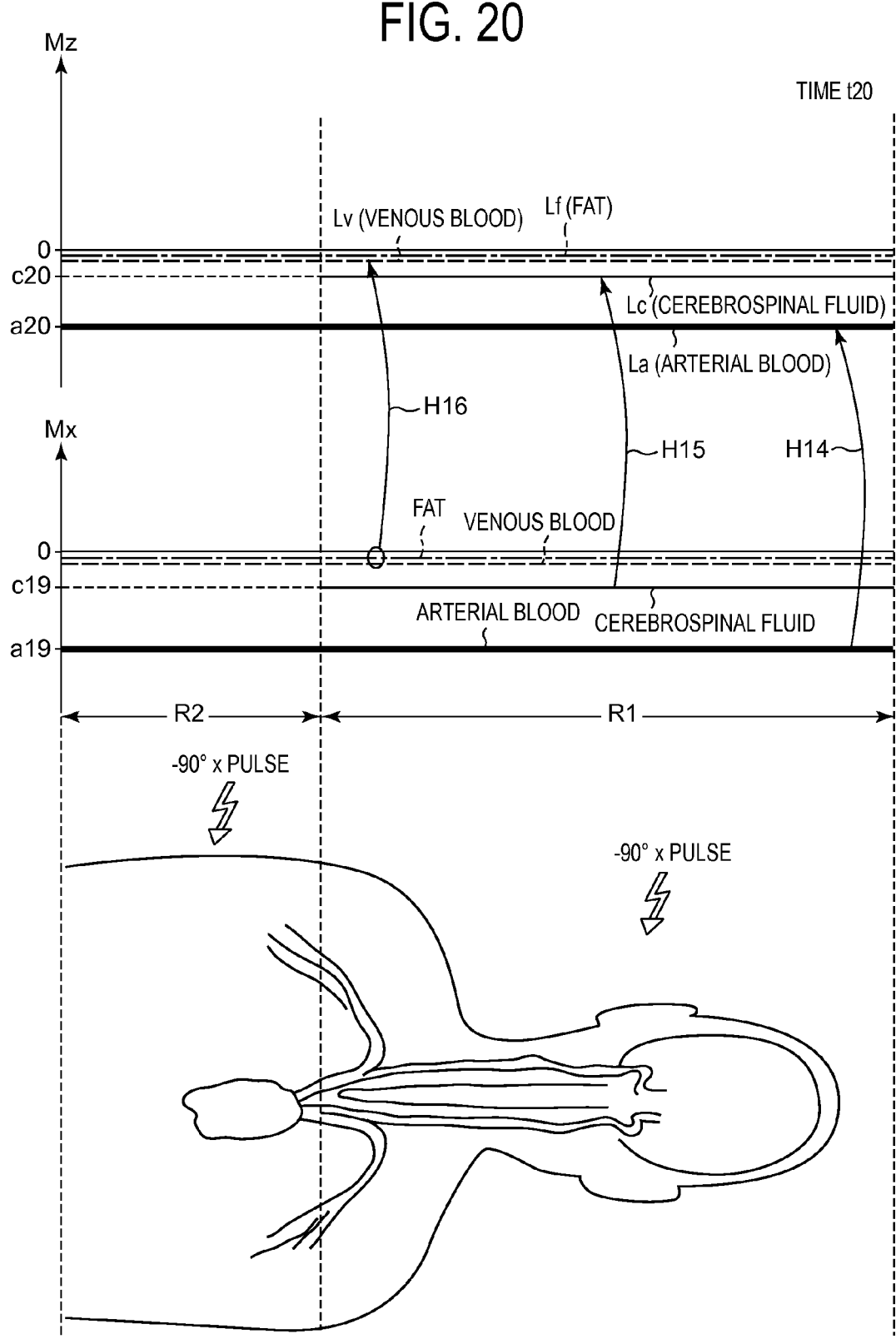
FIG. 20 is a diagram for describing how the magnetization of arterial blood, cerebrospinal fluid, fat and venous blood lying within the imaging surface change according to a $-90°$ x pulse (time t20).

FIG. 20 is a diagram for describing how the magnetization of arterial blood, cerebrospinal fluid, fat and venous blood lying within the imaging surface change according to the −90° x pulse (time t20).

A graph indicative of longitudinal magnetization Mz is shown on the top of FIG. 20, and a graph indicative of transverse magnetization Mx is shown therebelow.

The −90° x pulse is a non-selective pulse for flipping the transverse magnetization Mx to the longitudinal magnetization Mz. Thus, the transverse magnetization Mx=a19 of arterial blood in each of the regions R1 and R2 is flipped to longitudinal magnetization Mz=a20 by the transmission of the −90° x pulse (refer to arrow H4). The transverse magnetization Mx=c19 of cerebrospinal fluid is flipped to longitudinal magnetization Mz=c20 by the transmission of the −90° x pulse (refer to arrow H5). Since the transverse magnetization Mx of each of fat and venous blood is Mx≈0, the transverse magnetization Mx is flipped to longitudinal magnetization Mz≈0 (refer to arrow H6).

Even in FIGS. 13C and 13D, the manner in which the transverse magnetization Mx=a19 of arterial blood is flipped to the longitudinal magnetization Mz=a20 is indicated by the arrow H4, and the manner in which the transverse magnetization Mx=c19 of cerebrospinal fluid is flipped to the longitudinal magnetization Mz=c20 is indicated by the arrow H5. Further, the manner in which the transverse magnetization Mx≈0 of each of fat and venous blood is flipped to the longitudinal magnetization Mz≈0 is indicated by the arrow H6.

(8) Time t21

The 180° pulse for inverting the longitudinal magnetization Mz is transmitted at the time t21 lying immediately after the transmission of the −90° x pulse. With transmission of the 180° pulse, the longitudinal magnetization Mz of each of arterial blood and background tissues (cerebrospinal fluid, fat and venous blood) changes in the following manner (refer to FIG. 21).

Figure 21:
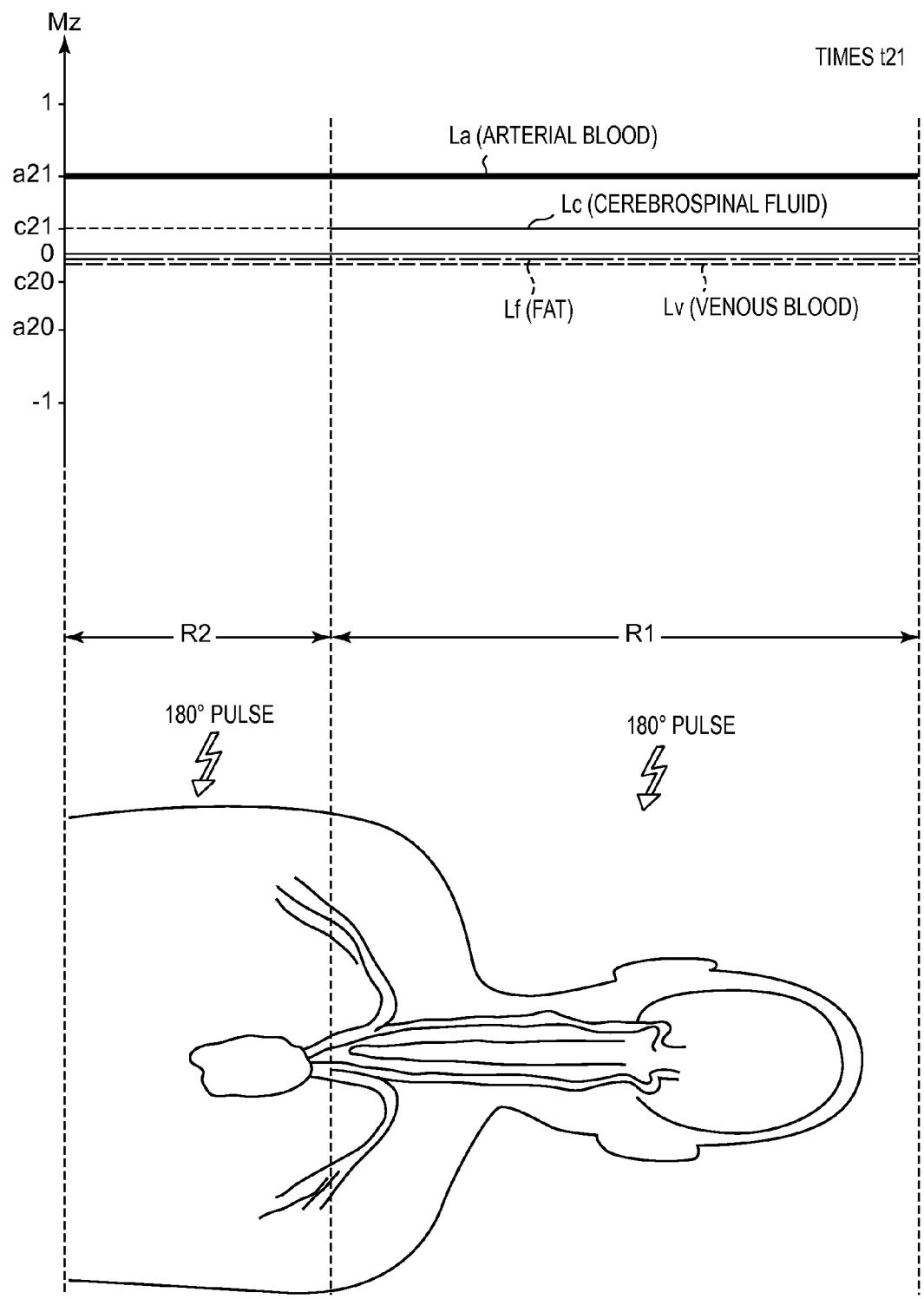
FIG. 21 is a diagram showing longitudinal magnetization Mz of arterial blood, cerebrospinal fluid, fat and venous blood lying within the imaging surface at a time t21.
Figure 22:
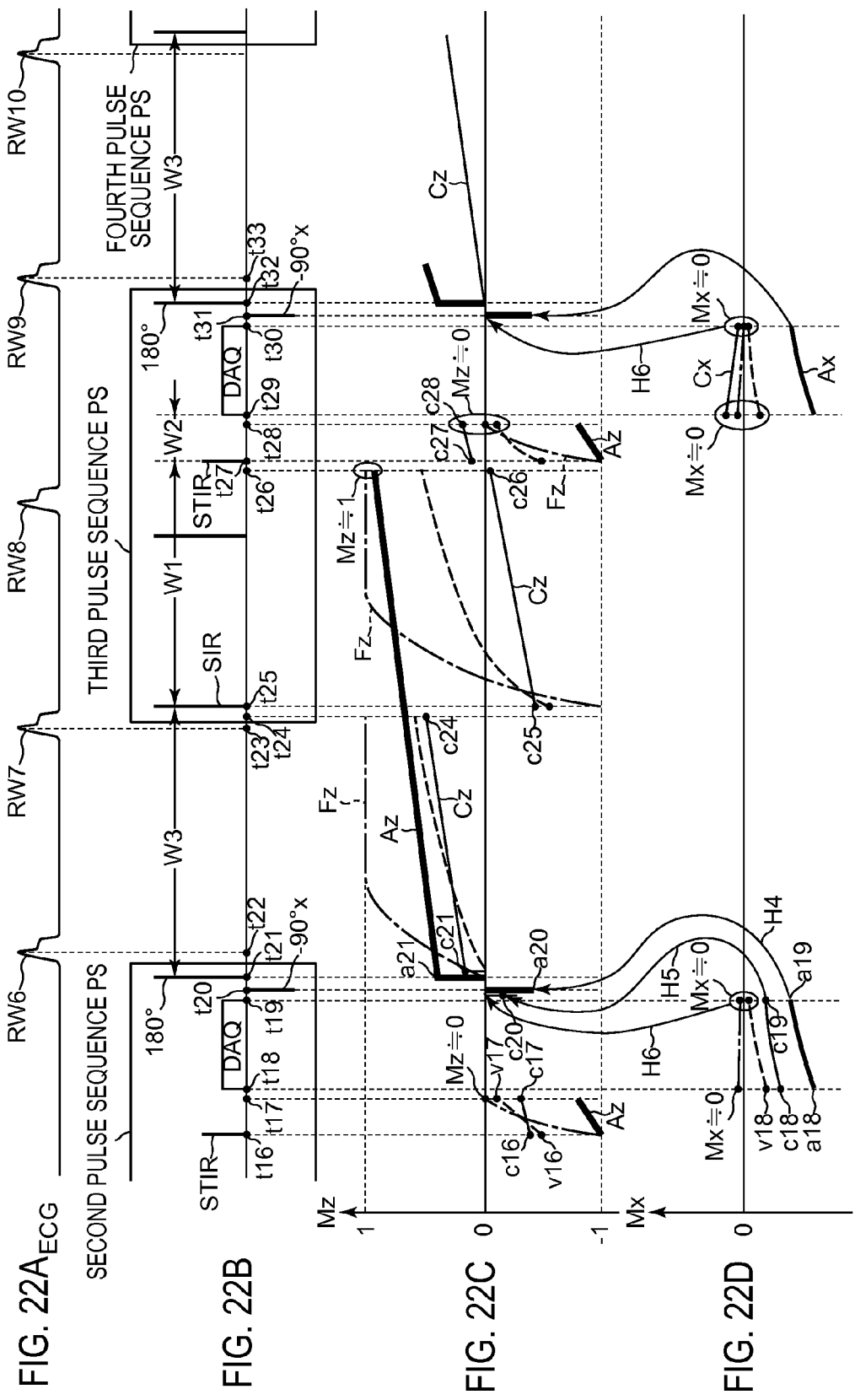
FIGS. 22A, 22B, 22C, and 22D are diagrams for describing how the magnetization of each tissue changes from the end of a second pulse sequence PS to the end of a third pulse sequence PS with a waiting time W3 interposed therebetween.

FIG. 21 is a diagram showing the longitudinal magnetization Mz of arterial blood, cerebrospinal fluid, fat and venous blood lying within the imaging surface at the time t21.

A description will be made below of how the longitudinal magnetization Mz of each of arterial blood and background tissues (cerebrospinal fluid, fat and venous blood) changes by the transmission of a 180° pulse while referring to FIG. 21.

(i) Longitudinal Magnetization Mz of Arterial Blood

The 180° pulse is of a non-selective pulse for inverting the longitudinal magnetization of the entire imaging surface. Thus, the longitudinal magnetization Mz of arterial blood in each of the regions R1 and R2 is inverted from Mz=a20 to Mz=a21 at the time t21 as shown in FIG. 21 (refer to the longitudinal magnetization recovery curve Az of FIG. 13C).

(ii) Longitudinal Magnetization Mz of Background Tissues (Cerebrospinal Fluid, Fat and Venous Blood)

The longitudinal magnetization Mz of cerebrospinal fluid in the region R1 is inverted from Mz=c20 to Mz=c21 by the transmission of the 180° pulse as shown in FIG. 21 (refer to the longitudinal magnetization recovery curve Cz of FIG. 13C).

Incidentally, since the longitudinal magnetization Mx of each of fat and venous blood is Mx≈0 at the time t20 (refer to FIG. 20), the longitudinal magnetization is Mz≈0 even at the time t21.

With the transmission of the 180° pulse at the time t21, the second pulse sequence PS is completed. After the completion of the second pulse sequence PS, the coil control device 61 detects two R waves RW6 and RW7 (times t22 and t23). After the second R wave RW7 has been detected by the coil control device 61, the coil control device 61 controls the gradient coil and the transmitting coil in synchronization with the R wave RW7 in such a manner that a third pulse sequence PS is started. Thus, a waiting time W3 is provided between the second pulse sequence PS and the third pulse sequence PS. A description will next be made of how the magnetization of each tissue changes till the completion of the third pulse sequence PS after the completion of the second pulse sequence PS with the waiting time W3 interposed therebetween.

FIGS. 22A-22D are diagrams for describing how the magnetization of each tissue changes from the end of a second pulse sequence PS to the end of a third pulse sequence PS with a waiting time W3 interposed therebetween.

A description will hereinafter be made of the behaviors of magnetization of arterial blood and background tissues (cerebrospinal fluid, fat and venous blood) from the end of the second pulse sequence PS to the end of the third pulse sequence PS (times t21 to t32) while referring to FIGS. 22A-22D. Incidentally, since the behaviors of the magnetization of arterial blood, fat and venous blood are approximately identical to the behaviors (times t10 to t21) from the end of the first pulse sequence PS to the end of the second pulse sequence PS, only the behavior of magnetization of cerebrospinal fluid will be explained in the following description.

(1) Times t21 to t24

After the 180° pulse has been transmitted at the time t21, a waiting time W3 (refer to FIG. 22B) is provided until the third pulse sequence PS is started. Thus, the longitudinal magnetization of cerebrospinal fluid proceeds in longitudinal relaxation during the waiting time W3 and is recovered to Mz=c24 at the time t24 lying immediately before a selective inversion pulse SIR for the third pulse sequence PS is transmitted (refer to a longitudinal magnetization recovery curve Cz of FIG. 22C).

(2) Time t25

At the time t25, the selective inversion pulse SIR (refer to FIG. 22B) for the third pulse sequence PS is transmitted. The longitudinal magnetization Mz of cerebrospinal fluid is inverted from Mz=c24 to Mz=c25 by the transmission of the selective inversion pulse SIR.

(3) Times t25 to t26

After the selective inversion pulse SIR has been transmitted at the time t25, a fat suppression pulse STIR is transmitted at the time t27. A waiting time W1 is however provided between the times t25 and t27. Thus, longitudinal relaxation proceeds during a waiting time W1, and the longitudinal magnetization Mz of cerebrospinal fluid is recovered to Mz=c26 at the time t26 lying immediately before the transmission of the fat suppression pulse STIR. Mz=c26 is Mz≈0.

(4) Time t27

At the time t27, the fat suppression pulse STIR (refer to FIG. 22B) is transmitted. With the transmission of the fat suppression pulse STIR, the longitudinal magnetization Mz of cerebrospinal fluid is inverted from Mz=c26 to Mz=c27.

(5) Times t27 to t28

After the transmission of the fat suppression pulse STIR at the time t27, signal acquisition is started at the time t29. A waiting time W2 is however provided between the times t27 and t29 (refer to FIG. 22B). Thus, longitudinal relaxation proceeds during the waiting time W2, and the longitudinal magnetization Mz of cerebrospinal fluid is recovered from Mz=c27 to Mz=c28 at the time t28 lying immediately before the start of the signal acquisition. Since, however, the T1 value of cerebrospinal fluid is long (4 sec or so), the amount of recovery of the longitudinal magnetization of cerebrospinal fluid during the waiting time W2 is of a negligible value. Accordingly, Mz=c28 is Mz≈0.

Figure 23:
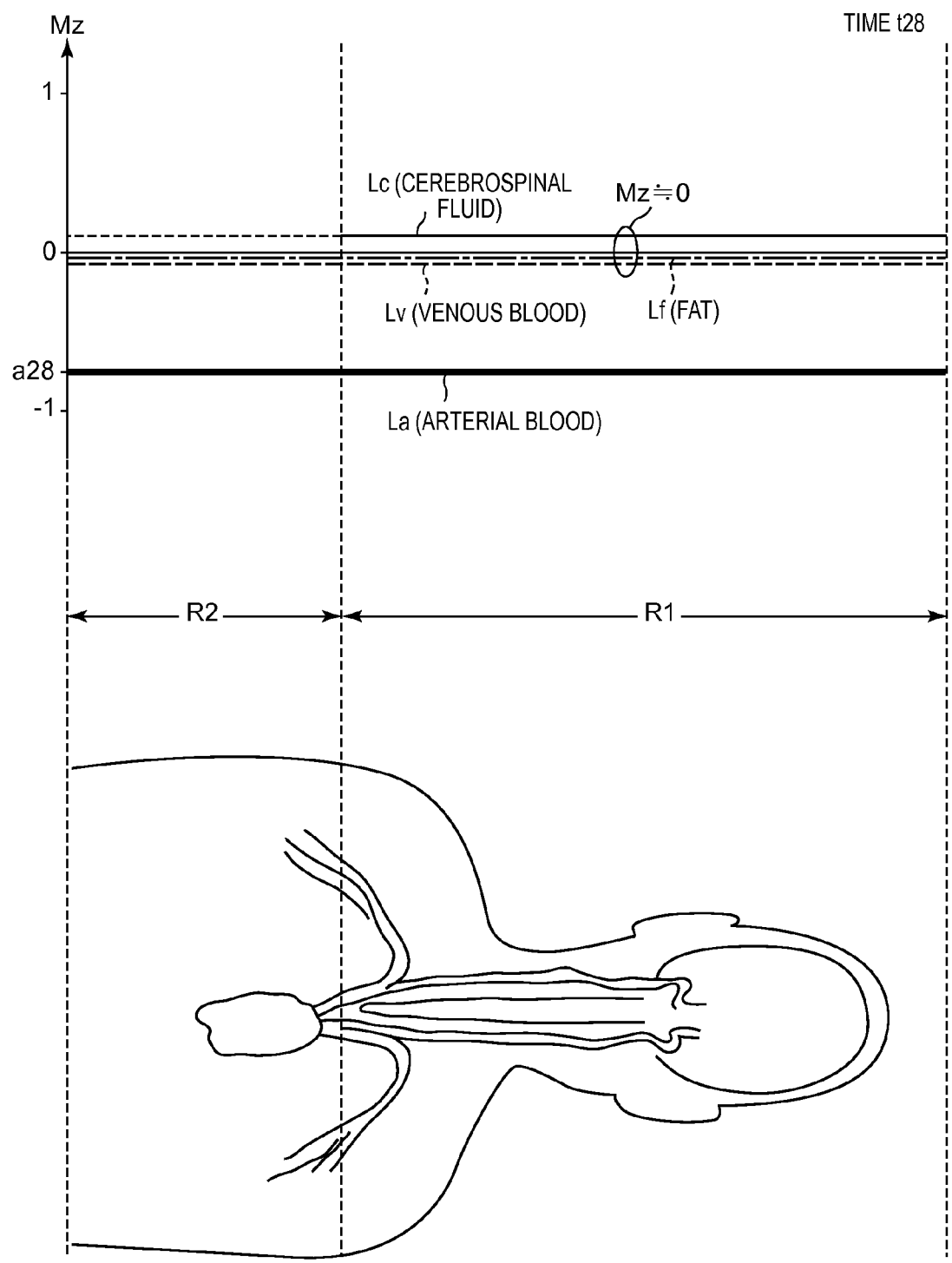
FIG. 23 is a diagram showing longitudinal magnetization Mz of arterial blood, cerebrospinal fluid, fat and venous blood lying within the imaging surface at a time t28.

FIG. 23 is a diagram showing longitudinal magnetization Mz of arterial blood, cerebrospinal fluid, fat and venous blood lying within the imaging surface at the time t28.

It is understood that referring to FIG. 23, the longitudinal magnetization Mz of arterial blood has a sufficiently large negative value, whereas the longitudinal magnetization Mz of each of background tissues (cerebrospinal fluid, fat and venous blood) is Mz≈0.

(6) Times t29 to t30

A signal acquisition sequence DAQ for acquiring magnetic resonance signals is executed between the times t29 and t30. While the signal acquisition sequence DAQ is being executed, the longitudinal magnetization Mz of cerebrospinal fluid becomes a value close to Mz=0 (null point). The transverse magnetization Mx of cerebrospinal fluid becomes a value close to the null point between the signal acquisition times t29 and t30 (refer to the transverse magnetization curve Cx).

Incidentally, the longitudinal magnetization Mz (=c28) of cerebrospinal fluid at the time t28 lying immediately before the start of signal acquisition becomes Mz≈0 in the third pulse sequence PS. Thus, even though the magnetic resonance signals for embedding a low-frequency region in a k space are acquired between the times t29 and t30, an image in which the cerebrospinal fluid is sufficiently suppressed can be obtained.

(7) Times t31 and t32

At the times t31 and t32 lying immediately after the signal acquisition has been done, a −90° x pulse and a 180° pulse are transmitted. Since, however, the transverse magnetization Mx of cerebrospinal fluid at the signal acquisition time t30 is Mz≈0, the longitudinal magnetization Mz of cerebrospinal fluid is Mz≈0 at the times t31 and t32 even though the −90° x pulse and 180° pulse are transmitted. With the transmission of the 180° pulse at the time t32, the third pulse sequence PS is completed. After the completion of the third pulse sequence, a fourth pulse sequence PS is started with a waiting time W3 interposed therebetween. During the waiting time W3, the longitudinal magnetization Mz of cerebrospinal fluid proceeds in longitudinal relaxation and is recovered gradually (refer to the longitudinal relaxation curve Cz of 22C).

Pulse sequences PS are repeatedly executed in like manner subsequently while the waiting time W3 is being interposed therebetween.

In the present embodiment, the operator 10 operates the input device 7 to input an imaging command where the subject 9 is imaged. In response to the imaging command, the coil control device 61 (refer to FIG. 1) controls the gradient coil 23 and the transmitting coil 24 based on the electrocardiac signal ECG outputted from the heartbeat sensor 4 in such a manner that the pulse sequence PS (refer to FIG. 3(b)) is repeatedly executed. When the pulse sequence PS is executed, the longitudinal magnetization Mz of each of background tissues (fat and venous blood) short in T1 value becomes a value close to the null point at the time t6 lying immediately before the signal acquisition for the first pulse sequence PS as described while referring to FIGS. 3 through 23. In contrast, the longitudinal magnetization Mz of background tissue (cerebrospinal fluid) long in T1 value becomes a relatively large positive value (Mz=c6) at the time t6 lying immediately before the signal acquisition for the first pulse sequence PS. Thus, the mere execution of the first pulse sequence PS makes it unable to obtain an image in which the background tissue (cerebrospinal fluid) long in T1 value has been sufficiently suppressed. However, the longitudinal magnetization Mz of background tissue (cerebrospinal fluid) long in T1 value can also be made close to the null point by executing the pulse sequence PS repeatedly. In the present embodiment, the longitudinal magnetization Mz of background tissue (cerebrospinal fluid) long in T1 value as well as the longitudinal magnetization Mz of each of background tissues (fat and venous blood) short in T1 value can be set to a value sufficiently close to the null point at the time t28 lying immediately before the start of signal acquisition for the third pulse sequence PS. Once the longitudinal magnetization Mz of background tissue (cerebrospinal fluid) long in T1 value is brought to the value close to the null point, the longitudinal magnetization Mz becomes a value close to the null point even at a time lying immediately before signal acquisition for a pulse sequence PS executed subsequently to the above sequence. Thus, the pulse sequence PS employed in the present embodiment is repeatedly executed thereby to enable the acquisition of an image in which both a background tissue short in T1 value and a background tissue long in T1 value are sufficiently suppressed and the arterial blood is visualized, even though a difference image is not generated, thus making it possible to achieve the shortening of an imaging time.

Incidentally, while the longitudinal magnetization Mz of each of fat and venous blood at the time t6 immediately before the signal acquisition is of the value close to Mz=0 in the first pulse sequence PS as shown in FIG. 4, the longitudinal magnetization Mz of cerebrospinal fluid has the relatively large positive value (Mz=c6). Thus, there is a possibility that an image in which the cerebrospinal fluid is visualized emphatically in addition to the arterial blood will be obtained where the magnetic resonance signals for embedding the low-frequency region in the k space are acquired between the signal acquisition times t7 and t8 for the first pulse sequence PS. It is therefore desired that in the first pulse sequence PS, magnetic resonance signals for embedding a high-frequency region in the k space are acquired or the acquired magnetic resonance signals are not used as data for image reconstruction.

Referring to FIG. 13, the longitudinal magnetization Mz (=c17) of cerebrospinal fluid at the time t17 lying immediately before the signal acquisition for the second pulse sequence PS is closer to the null point than the longitudinal magnetization Mz (=c6) of cerebrospinal fluid at the time t6 lying immediately before the signal acquisition for the first pulse sequence PS. Thus, even though the magnetic resonance signals for embedding the low-frequency region in the k space are collected in the second pulse sequence PS, an image in which the cerebrospinal fluid is suppressed to some degree is obtained. Since, however, the longitudinal magnetization Mz of cerebrospinal fluid immediately before the signal acquisition becomes Mz=0 in the third pulse sequence PS as described above (refer to FIGS. 22 and 23), the magnetic resonance signals for embedding the high-frequency region in the k space are acquired in the second pulse sequence PS and the magnetic resonance signals for embedding the low-frequency signal in the k space may be acquired in the third pulse sequence PS.

In the present embodiment, the pulse sequence PS is started in synchronization with each R wave of the electrocardiac signal ECG. Thus, the value of the waiting time W3 also varies according to the length of the R-to-R interval (interval between R waves) of the electrocardiac signal ECG. Since the amount of recovery of the longitudinal magnetization Mz of cerebrospinal fluid between the waiting times W3 differs when the value of the waiting time W3 varies, the values of the longitudinal magnetization Mz of cerebrospinal fluid at the times (t17, t28 and the like) immediately before the signal acquisition become values that differ according to the length of the waiting time W3. For example, the longer the length of the waiting time W3, the more the longitudinal magnetization Mz of cerebrospinal fluid at each time lying immediately before the signal acquisition gradually increases and deviates from the null point. When the longitudinal magnetization Mz of cerebrospinal fluid at each time lying immediately before the signal acquisition deviates excessively from the null point, it becomes difficult to obtain an image in which the cerebrospinal fluid is sufficiently suppressed. It is thus desired that even though the value of the waiting time W3 varies, the longitudinal magnetization Mz of cerebrospinal fluid at each time immediately before the signal acquisition is prevented from excessively deviating from the null point. Therefore, in the present embodiment, each pulse sequence PS is provided with the two RF pulses (−90° x pulse and 180° pulse) immediately after the signal acquisition sequence DAQ. With the provision of the two RF pulses (−90° x pulse and 180° pulse) in the pulse sequence PS immediately after the signal acquisition sequence DAQ, the longitudinal magnetization Mz of cerebrospinal fluid at the time lying immediately before the signal acquisition can be prevented from excessively deviating from the null point even though the value of the waiting time W3 varies. In order to explain this reason, a description will be made of how the magnetization of cerebrospinal fluid changes according to the presence or absence of the two RF pulses (−90° x pulse and 180° pulse) immediately after the signal acquisition sequence DAQ. Incidentally, the waiting time W3 will be explained below in two parts: (1) W3=1200 msec and (2) W3=4000 msec.

(1) Waiting time W3=1200 msec

FIGS. 24A-24C are diagrams for describing how the magnetization of cerebrospinal fluid changes from the end of a first pulse sequence PS to the end of a second pulse sequence PS with a waiting time W3 (=1200 msec) interposed therebetween.

Longitudinal and transverse magnetization recovery curves Cz and Cx of cerebrospinal fluid, and longitudinal and transverse magnetization recovery curves Ez and Ex of cerebrospinal fluid are shown in FIGS. 24A-24C. The magnetization recovery curves Cz and Cx (indicated by solid lines) respectively show the behaviors of magnetization of cerebrospinal fluid where two RF pulses (−90° x pulse and 180° pulse) are transmitted immediately after a signal acquisition sequence DAQ. On the other hand, the magnetization recovery curves Ez and Ex (indicated by broken lines) respectively show the behaviors of magnetization of cerebrospinal fluid where two RF pulses (−90° x pulse and 180° pulse) are not transmitted immediately after a signal acquisition sequence DAQ.

Since the magnetization recovery curves Cz and Cx are identical to the magnetization recovery curves Cz and Cx shown in FIG. 13C, the explanations of the magnetization recovery curves Cz and Cx are omitted and other magnetization recovery curves Ez and Ex will be explained.

When the two RF pulses (−90° x pulse and 180° pulse) are not transmitted immediately after a signal acquisition sequence DAQ, the longitudinal magnetization Mz of cerebrospinal fluid is Mz=0 at a time t8 but gradually recovered from Mz≈0 (refer to the longitudinal magnetization recovery curve Ez). It is thus understood that when the two magnetization recovery curves Cz and Ez are compared, the longitudinal magnetization begins to recover from a relatively large negative value (Mz=c10) at a time t10 in the magnetization recovery curve Cz, whereas the longitudinal magnetization begins to recover from the neighborhood of the null point (Mz≈0) at the signal acquisition end time t8 in the magnetization recovery curve Ez.

The longitudinal magnetization Mz of cerebrospinal fluid, which has begun to recover from the null point, is recovered to Mz=e13 at a time t13 lying immediately before a selective inversion pulse SIR for the second pulse sequence PS is transmitted. Thus, the longitudinal magnetization Mz is inverted from Mz=e13 to Mz=e14 by the transmission of the selective inversion pulse SIR. Thereafter, the longitudinal magnetization Mz of cerebrospinal fluid is gradually recovered and becomes a value e17 close to the null point at a time t17 lying immediately before signal acquisition. After the execution of the second pulse sequence PS, a third pulse sequence PS is executed.

Figures 25A, 25B, 25C:
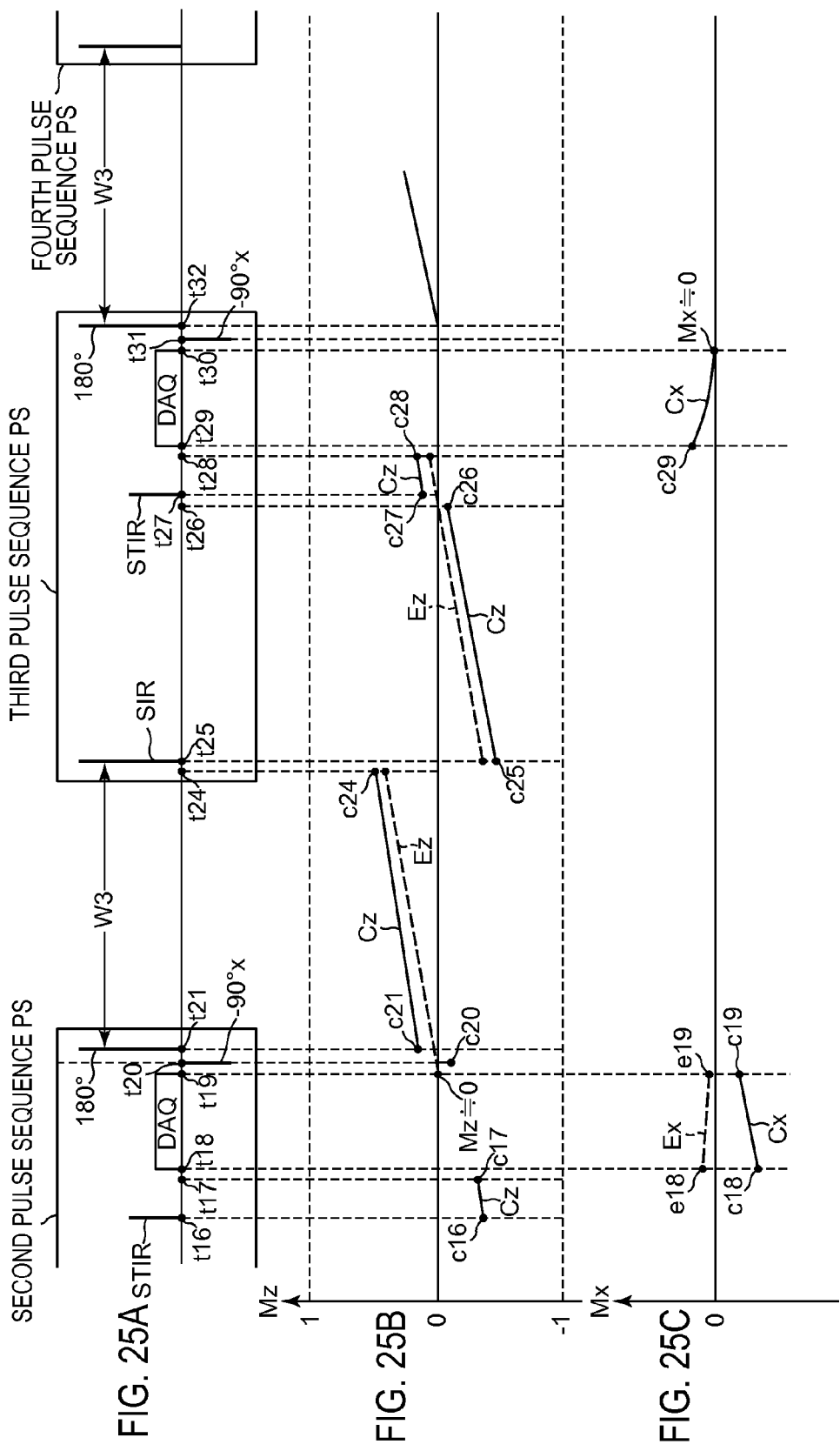
FIGS. 25A, 25B, and 25C are diagrams for describing how the magnetization of cerebrospinal fluid changes from the end of a second pulse sequence PS to the end of a third pulse sequence PS with a waiting time W3 interposed therebetween.

FIGS. 25A-25C are diagrams for describing how the magnetization of cerebrospinal fluid changes from the end of a second pulse sequence PS to the end of a third pulse sequence PS with a waiting time W3 interposed therebetween.

The magnetization recovery curve Ez shows a magnetization recovery similar to FIG. 24B even during a period from the end of the second pulse sequence PS to the end of the third pulse sequence PS. Thus, the longitudinal magnetization Mz of cerebrospinal fluid becomes a value close to the null point even at a time t28 lying immediately before the signal acquisition for the third pulse sequence PS. It is understood that both the magnetization recovery curves Cz and Ez reach positions each close to the null point at the time t28 lying immediately before the signal acquisition for the third pulse sequence PS.

Thus, when the waiting time W3=1200 msec, the longitudinal magnetization Mz of cerebrospinal fluid immediately before the signal acquisition becomes Mz≈0 subsequently to the third pulse sequence PS regardless of the presence or absence of the two RF pulses (−90° x pulse and 180° pulse).

(2) Waiting time W3=4000 msec

FIGS. 26A-26C are diagrams for describing how the magnetization of cerebrospinal fluid changes from the end of a first pulse sequence PS to the end of a second pulse sequence PS with a waiting time W3 (=4000 msec) interposed therebetween.

Magnetization recovery curves Cz and Cz, and Ez and Ex of cerebrospinal fluid are shown in FIGS. 26A-26C. The magnetization recovery curves Cz and Cx (indicated by solid lines) respectively show the behaviors of magnetization of cerebrospinal fluid where two RF pulses (−90° x pulse and 180° pulse) are transmitted immediately after a signal acquisition sequence DAQ. On the other hand, the magnetization recovery curves EZ and Ex (indicated by broke lines) respectively show the behaviors of magnetization of cerebrospinal fluid where two RF pulses (−90° x pulse and 180° pulse) are transmitted immediately after a signal acquisition sequence DAQ.

When the two RF pulses (−90° x pulse and 180° pulse) are transmitted immediately after the signal acquisition sequence DAQ, the longitudinal magnetization Mz of cerebrospinal fluid is Mz=c10 at a time t10 but is recovered gradually from Mz=10 (refer to the magnetization recovery curve Cz). Since, however, the waiting time W3 is long like W3=4000 msec, the longitudinal magnetization Mz of cerebrospinal fluid is recovered to Mz=c13 by a time t13.

After the longitudinal magnetization Mz of cerebrospinal fluid has been recovered to Mz=c13, the longitudinal magnetization Mz is inverted from Mz=c13 to Mz=c14 by a selective inversion pulse SIR for the second pulse sequence PS. Thereafter, the longitudinal magnetization Mz of cerebrospinal fluid is recovered to Mz=c15 up to a time t15 lying immediately before the transmission of a fat suppression pulse STIR. The longitudinal magnetization of cerebrospinal fluid Mz=c15 is inverted from Mz=c15 to Mz=c16 by the fat suppression pulse STIR and recovered to Mz=c17 by a time t17 lying immediately before signal acquisition. The transverse magnetization Mx of cerebrospinal fluid is gradually reduced between signal acquisition times t18 and t19 (refer to the transverse magnetization recovery curve Cx). After the signal acquisition sequence DAQ has been completed, the longitudinal magnetization Mz of cerebrospinal fluid becomes Mz=c21 by the two RF pulses (−90° x pulse and 180° pulse).

On the other hand, when the two RF pulses (−90° x pulse and 180° pulse) are not transmitted immediately after the signal acquisition sequence DAQ, the longitudinal magnetization Mz of cerebrospinal fluid is Mz≈0 at a time t8 but is gradually recovered from Mz≈0. The longitudinal magnetization Mz is recovered to a value e13 close to Mz=1 at the time t13 lying immediately before the transmission of the selective inversion pulse SIR (refer to the longitudinal magnetization recovery curve Ez). Thus, the magnetization recovery curve Ez is recovered greater by ΔM1 than the magnetization recovery curve Cz at the time t13. The longitudinal magnetization Mz=e13 of cerebrospinal fluid is inverted from Mz=e13 to Mz=e14 by the transmission of the selective inversion pulse SIR. Thereafter, the longitudinal magnetization Mz of cerebrospinal fluid is gradually recovered and inverted by the corresponding fat suppression pulse STIR, thus reaching Mz=e17 at the time t17 lying immediately before the signal acquisition. After the second pulse sequence PS has been executed, a third pulse sequence PS is executed. It is thus understood that the magnetization recovery curve Ez becomes a value larger by ΔM2 than the magnetization recovery curve Cz at the time t17 lying immediately before the signal acquisition.

FIGS. 27A-27C are diagrams for describing how the magnetization of cerebrospinal fluid changes from the end of a second pulse sequence PS to the end of a third pulse sequence PS with a waiting time W3 (=4000 msec) interposed therebetween.

When two RF pulses (−90° x pulse and 180° pulse) are transmitted immediately after a signal acquisition sequence DAQ, the longitudinal magnetization Mz of cerebrospinal fluid is Mz=c21 at a time t21 but is gradually recovered from Mz=c21 (refer to the longitudinal magnetization recovery curve Cz). Since, however, the waiting time W3 is long like W3=4000 msec, the longitudinal magnetization Mz of cerebrospinal fluid is recovered to Mz=c24 by a time t24.

After the longitudinal magnetization Mz of cerebrospinal fluid has been recovered to Mz=c24, the longitudinal magnetization Mz is inverted from Mz=c24 to Mz=c25 by a selective inversion pulse SIR for the second pulse sequence PS. Thereafter, the longitudinal magnetization Mz of cerebrospinal fluid is recovered to Mz=c26 by a time t26 lying immediately before the transmission of a fat suppression pulse STIR. The longitudinal magnetization Mz=c26 of cerebrospinal fluid is inverted from Mz=c26 to Mz=c27 by the fat suppression pulse STIR and recovered to Mz=c28 by a time t28 lying immediately before signal acquisition.

On the other hand, when the two RF pulses (−90° x pulse and 180° pulse) are not transmitted immediately after the signal acquisition sequence DAQ, the magnetization recovery curve Ez indicates a magnetization recovery similar to FIG. 26. It is thus understood that the magnetization recovery curve Ez is recovered greater by ΔM3 than the magnetization recovery curve Cz at the time t24 and further the magnetization recovery curve Ez becomes a value larger by ΔM2 than the magnetization recovery curve Cz at the time t28 lying immediately before the signal acquisition.

Referring to FIG. 26, the magnetization recovery curve Ez begins to recover from the null point at the time t8, whereas the magnetization recovery curve Cz begins to recover from a negative value (Mz=c10) at the time t10. Thus, the longitudinal magnetization c13 of the magnetization recovery curve Cz becomes closer to the null point by ΔM1 than the longitudinal magnetization e13 of the magnetization recovery curve Ez. After the longitudinal magnetization c13 of the magnetization recovery curve Cz is made closer to the null point by ΔM1 than the longitudinal magnetization e13 of the magnetization recovery curve Ez, a selective inversion pulse SIR (time t14) and a fat suppression pulse STIR (time t16) are transmitted. Thus, the longitudinal magnetization recovery curve Cz varies in a region closer to the null point than the longitudinal magnetization recovery curve Ez from the transmission of the selective inversion pulse SIR (time t14) to immediately before the acquisition of magnetic resonance signals (time t17). Therefore, the two RF pulses (−90° x pulse and 180° pulse) are transmitted immediately after the signal acquisition sequence DAQ thereby to make it possible to prevent the longitudinal magnetization Mz of cerebrospinal fluid immediately before the signal acquisition from excessively deviating from the null point regardless of the value of the waiting time W3. Further, simulation was performed to verify advantages of the two RF pulses (−90° x pulse and 180° pulse). The results of simulation will next be explained.

Figure 28:
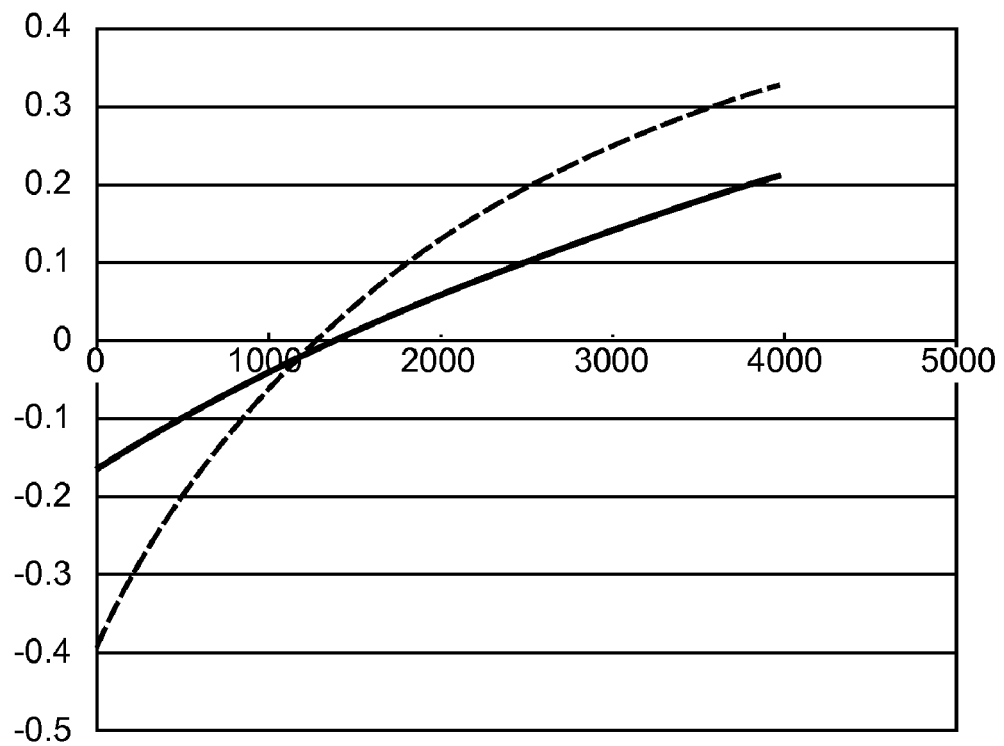
FIG. 28 is a graph illustrating simulation results.

FIG. 28 is a graph showing the results of simulation.

The horizontal axis of the graph shown in FIG. 28 indicates a waiting time W3, and the vertical axis thereof indicates longitudinal magnetization Mz of cerebrospinal fluid immediately before signal acquisition. A solid line of the graph indicates the longitudinal magnetization Mz of cerebrospinal fluid immediately before the signal acquisition at the time that the pulse sequence PS of the present embodiment is repeated four times. A broken line of the graph indicates the longitudinal magnetization Mz of cerebrospinal fluid immediately before the signal acquisition at the time that the two RF pulses (−90° x pulse and 180° pulse) are not transmitted.

It is understood from the graph shown in FIG. 28 that the longitudinal magnetization Mz of cerebrospinal fluid immediately before the signal acquisition approaches the null point by the transmission of the two RF pulses (−90° x pulse and 180° pulse) as compared with the case in which the two RF pulses (−90° x pulse and 180° pulse) are not transmitted.

Incidentally, in the present embodiment, the pulse sequence PS having the two RF pulses (−90° x pulse and 180° pulse) immediately after the signal acquisition sequence DAQ is used. Another pulse sequence may however be used instead of the pulse sequence PS.

Figure 29:
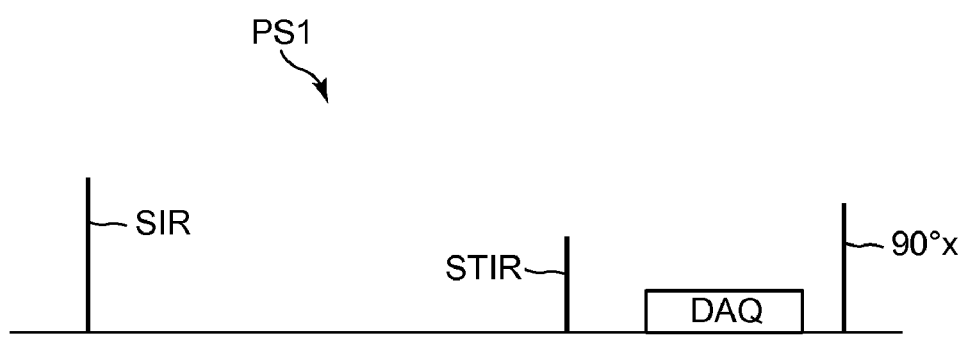
FIG. 29 is one example of another pulse sequence.

FIG. 29 is one example of another pulse sequence.

The pulse sequence PS1 is provided with a 90° x pulse alone immediately after a signal acquisition sequence DAQ as an alternative to the two RF pulses (−90° x pulse and 180° pulse). A description will be made of how the magnetization of each tissue changes where the 90° x pulse is provided.

FIGS. 30A-30D are diagrams showing the behaviors of magnetization of arterial blood and background tissues (cerebrospinal fluid, fat and venous blood) where the pulse sequence PS1 shown in FIG. 29 is used.

The behaviors of magnetization of respective tissues from in the middle of the first pulse sequence PS1 to the end of a second pulse sequence PS1 are shown in FIG. 30B.

The 90° x pulse is a pulse for flipping the transverse magnetization of each tissue to the longitudinal magnetization in a manner similar to the −90° x pulse. However, the 90° x pulse flips the transverse magnetization in the direction opposite to the −90° x pulse. Thus, even though only the 90° x pulse is transmitted immediately after the signal acquisition sequence DAQ, an advantageous effect similar to the case where the two RF pulses (−90° x pulse and 180° pulse) are transmitted can be obtained. Since, however, an ununiform effect on a static magnetic field can be reduced where the two RF pulses (−90° x pulse and 180° pulse) are transmitted, the two RF pulses (−90° x pulse and 180° pulse) are preferably transmitted as compared with the transmission of only the 90° x pulse.

Incidentally, there are shown in the above description, the example in which the two RF pulses (−90° x pulse and 180° pulse) are transmitted immediately after the signal acquisition sequence DAQ, and the example in which only the 90° x pulse is transmitted immediately thereafter. A 90° y pulse, a −90° y pulse, etc. may however be used according to the type of signal acquisition sequence DAQ instead of the −90° x pulse and the 90° x pulse. Further, the 90° y pulse, −90° y pulse and the like can also be used together with the −90° x pulse and the 90° x pulse.

In the present embodiment, the fat suppression pulse STIR, −90° x pulse and 180° pulse are non-selective pulses. If, however, the advantage of the invention is obtained, then a selective pulse may be adopted. The non-selective pulse can also be used instead of the selective inversion pulse SIR.

Further, although the cerebrospinal fluid, fat and venous blood are shown as the background tissues in the present embodiment, other background tissues such as muscles can be suppressed by using the present embodiment.

Many widely different embodiments of the invention may be configured without departing from the spirit and the scope of the present invention. It should be understood that the present invention is not limited to the specific embodiments described in the specification, except as defined in the appended claims.

What is claimed is:

1. A magnetic resonance imaging apparatus comprising:
a gradient coil configured to apply a gradient pulse;
a transmitting coil configured to transmit a radio frequency (RF) pulse; and
a coil control device configured to control the gradient coil and the transmitting coil such that a first pulse sequence is executed to:
make an absolute value of longitudinal magnetization of a first background tissue and an absolute value of longitudinal magnetization of a second background tissue longer in T1 value than the first background tissue smaller than an absolute value of longitudinal magnetization of arterial blood of a subject;
acquire magnetic resonance signals from the subject;
set, using a first RF pulse, the longitudinal magnetization of the second background tissue existing in a first region to a positive value and set the longitudinal magnetization of the arterial blood existing in a second region to a negative value; and
set, using a second RF pulse, the longitudinal magnetization of the second background tissue existing in the first region to a negative value that approaches null during a waiting time between the first and second RF pulses, and set the longitudinal magnetization of the arterial blood existing in the second region to a positive value.

2. The magnetic resonance imaging apparatus according to claim 1, wherein the coil control device is configured to control the gradient coil and the transmitting coil such that a second pulse sequence is executed after each execution of the first pulse sequence to:
make the longitudinal magnetization of the first background tissue existing in the first region to a negative value;
enable the arterial blood to flow from the second region to the first region and thereafter acquiring magnetic resonance signals from the subject; and
flip the transverse magnetization of the second background tissue existing in the first region to longitudinal magnetization.

3. The magnetic resonance imaging apparatus according to claim 2, wherein the second pulse sequence includes:
a signal acquisition sequence for acquiring the magnetic resonance signals from the subject;
a first RF pulse for, after the signal acquisition sequence, setting the longitudinal magnetization of the second background tissue existing in the first region to a positive value and setting the longitudinal magnetization of the arterial blood existing in the second region to a negative value; and
a second RF pulse for, after the first RF pulse, setting the longitudinal magnetization of the second background tissue existing in the first region to a negative value and setting the longitudinal magnetization of the arterial blood existing in the second region to a positive value.

4. The magnetic resonance imaging apparatus according to claim 3, wherein the first RF pulse is a −90° x pulse for flipping transverse magnetization to longitudinal magnetization, and wherein the second RF pulse is an inversion pulse.

5. The magnetic resonance imaging apparatus according to claim 4, wherein the second pulse sequence includes:
a third RF pulse for inverting the longitudinal magnetization of the first background tissue existing in the first region before the signal acquisition sequence; and
a fourth RF pulse for inverting the longitudinal magnetization of the first background tissue existing in the first region before the signal acquisition sequence after the third RF pulse.

6. The magnetic resonance imaging apparatus according to claim 3, wherein the second pulse sequence includes:
a third RF pulse for inverting the longitudinal magnetization of the first background tissue existing in the first region before the signal acquisition sequence; and
a fourth RF pulse for inverting the longitudinal magnetization of the first background tissue existing in the first region before the signal acquisition sequence after the third RF pulse.

7. The magnetic resonance imaging apparatus according to claim 2, wherein the coil control device is configured to control the gradient coil and the transmitting coil such that the second pulse sequence further includes a third RF pulse for setting the longitudinal magnetization of the second background tissue existing in the first region to a negative value and setting the longitudinal magnetization of the arterial blood existing in the second region to a positive value after the acquisition of the magnetic resonance signals from the subject.

8. The magnetic resonance imaging apparatus according to claim 7, wherein the third RF pulse of the second pulse sequence is a 90° x pulse for flipping transverse magnetization to longitudinal magnetization.

9. The magnetic resonance imaging apparatus according to claim 2, wherein the second pulse sequence includes:
a first RF pulse for inverting the longitudinal magnetization of the first background tissue existing in the first region before acquiring magnetic resonance signals; and
a second RF pulse for inverting the longitudinal magnetization of the first background tissue existing in the first region before acquiring magnetic resonance signals after the first RF pulse.

10. The magnetic resonance imaging apparatus according to claim 9, wherein during the second pulse sequence, a first waiting time is provided between the first RF pulse and the second RF pulse, and wherein a second waiting time is provided between the second RF pulse and the signal acquisition sequence.

11. The magnetic resonance imaging apparatus according to claim 10, wherein a third waiting time is provided between the first pulse sequence and the second pulse sequence.

12. The magnetic resonance imaging apparatus according to claim 1, wherein the first RF pulse is a −90° x pulse for flipping transverse magnetization to longitudinal magnetization, and wherein the second RF pulse is an inversion pulse.

13. The magnetic resonance imaging apparatus according to claim 12, wherein the first pulse sequence includes:
   a third RF pulse for inverting the longitudinal magnetization of the first background tissue existing in the first region before the signal acquisition sequence; and
   a fourth RF pulse for inverting the longitudinal magnetization of the first background tissue existing in the first region before the signal acquisition sequence after the third RF pulse.

14. The magnetic resonance imaging apparatus according to claim 1, wherein the coil control device is configured to control the gradient coil and the transmitting coil such that the first pulse sequence is further executed to set, using a third RF pulse, the longitudinal magnetization of the second background tissue existing in the first region to a negative value and set the longitudinal magnetization of the arterial blood existing in the second region to a positive value after the acquisition of the magnetic resonance signals from the subject.

15. The magnetic resonance imaging apparatus according to claim 14, wherein the third RF pulse of the first pulse sequence is a 90° x pulse for flipping transverse magnetization to longitudinal magnetization.

16. The magnetic resonance imaging apparatus according to claim 1, wherein the first pulse sequence includes:
   a third RF pulse for inverting the longitudinal magnetization of the first background tissue existing in the first region before the signal acquisition sequence; and
   a fourth RF pulse for inverting the longitudinal magnetization of the first background tissue existing in the first region before the signal acquisition sequence after the third RF pulse.

17. The magnetic resonance imaging apparatus according to claim 1, wherein a waiting time is provided between the first pulse sequence and the second pulse sequence that is executed after the first pulse sequence.

18. The magnetic resonance imaging apparatus according to claim 1, wherein the first background tissue is one of fat, a muscle and a vein, and wherein the second background tissue is cerebrospinal fluid.

19. A non-transitory computer-readable storage medium having computer-executable instructions embodied thereon for controlling a magnetic resonance imaging apparatus having a gradient coil configured to apply a gradient pulse and a transmitting coil configured to transmit a radio frequency (RF) pulse, wherein the magnetic resonance imaging apparatus includes a memory device and a processor, wherein when executed by the processor, the computer-executable instructions cause the processor to:
   repeatedly execute a pulse sequence to:
      make an absolute value of longitudinal magnetization of a first background tissue and an absolute value of longitudinal magnetization of a second background tissue longer in T1 value than the first background tissue, smaller than an absolute value of longitudinal magnetization of arterial blood of a subject;
   acquire magnetic resonance signals from the subject;
   set, using a first RF pulse, the longitudinal magnetization of the second background tissue existing in a first region to a positive value and set the longitudinal magnetization of the arterial blood existing in a second region to a negative value; and
   set, using a second RF pulse, the longitudinal magnetization of the second background tissue existing in the first region to a negative value that approaches null during a waiting time between the first and second RF pulses, and set the longitudinal magnetization of the arterial blood existing in the second region to a positive value.

\* \* \* \* \*